United States Patent [19]

Neuberger et al.

[11] Patent Number: 5,371,009
[45] Date of Patent: Dec. 6, 1994

[54] ENHANCERS

[75] Inventors: Michael S. Neuberger, Cambridge, United Kingdom; Kerstin B. Meyer, Marktschellenberg, Germany

[73] Assignee: Medical Research Council, London, United Kingdom

[21] Appl. No.: 768,437

[22] PCT Filed: Apr. 20, 1990

[86] PCT No.: PCT/GB90/00604
§ 371 Date: Sep. 25, 1991
§ 102(e) Date: Sep. 25, 1991

[87] PCT Pub. No.: WO90/12878
PCT Pub. Date: Nov. 1, 1990

[30] Foreign Application Priority Data

Apr. 22, 1989 [GB] United Kingdom ............ 8909218.3

[51] Int. Cl.$^5$ ............ C12N 5/00; C12N 15/00; C07H 21/00
[52] U.S. Cl. ............ 435/240.2; 435/172.3; 435/320.1; 536/24.1
[58] Field of Search ............ 800/2; 435/172.3, 69.6, 435/240.2; 514/44; 536/27, 24.1; 424/93

[56] References Cited

PUBLICATIONS

Peterson et al. Mol. Cell. Bul 7(12):4194, 1987.
Anderson et al. Science 226:401, 1984.
Stub et al. J. Exp. Med. 164:627, 1986.

*Primary Examiner*—Suzanne E. Ziska
*Attorney, Agent, or Firm*—Cushman Darby & Cushman

[57] ABSTRACT

A novel enhancer, known as the K3'-enhancer, has been identified in the mouse immunoglobulin K locus, downstream of $C_K$. The K3'-enhancer is B cell specific, is some sevenfold stronger than the K-intron enhancer and the region of the enhancer shows striking sequence homologies to the lymphotopic papovavirus, IgH and K-intron enhancers. The novel enhancer allows high level expression both in transfected cell lines and in transgenic mice, and may thus be used to enhance expression of genes in host cells, in vivo and in vitro. The novel enhancer is also found to increase somatic mutation of antibody genes in transgenic mice. The novel enhancer can also be use in gene therapy. Functionally equivalent enhancers are to be expected to occur downstream of $C_K$ of the immunoglobulin K locus of other species.

3 Claims, 31 Drawing Sheets

Fig. 3A

| Fig.3A1 |
|---|
| Fig.3A2 |

Fig. 3A1

```
001 AGCTCAAACC AGCTTAGGCT ACACAGAGAA ACTATCTAAA AAATAATTAC
    TAACTACTTA ATAGGAGATT GGATGTTAAG ATCTGGTCAC TAAGAGGCAG
101 AATTGAGATT CGAACCAGTA TTTTCTACCT GGTATGTTTT AAATTGCAGT
    AAGGATCTAA GTGTAGATAT ATAATAATAA GATTCTATTG ATCTCTGCAA
201 CAACAGAGAG TGTTAGATTT GTTTGGAAAA AAATATTATC AGCCAACATC
    TTCTACCATT TCAGTATAGC ACAGAGTACC CACCCATATC TCCCCACCCA
301 TCCCCCATAC CAGACTGGTT ATTGATTTTC ATGGTGACTG GCCTGAGAAG
    ATTAAAAAAA GTAATGCTAC CTTATTGGGA GTGTCCCATG GACCAAGATA
401 GCAACTGTCA TAGCTACCGT CACACTGCTT TGATCAAGAA GACCCTTTGA
    GGAACTGAAA ACAGAACCTT AGGCACATCT GTTGCTTTCG CTCCCATCCT
```

Fig. 3A2

```
501  CCTCCAACAG CCTGGGTGGT GCACTCCACA CCCTTTCAAG TTTCCAAAGC
     CTCATACACC TGCTCCCTAC CCCAGCACCT GGCCAAGGCT GTATCCAGCA
601  CTGGGATGAA AATGATACCC CACCTCCATC TTGTTTGATA TTACTCTATC
     TCAAGCCCCA GGTTAGTCCC CAGTCCCCAAT GCTTTTGCAC AGTCAAAACT
701  CAACTTGGAA TAATCAGTAT CCTTGAAGAG TTCTGATATG GTCACTGGGC
     CCATATACCA TGTAAGACAT GTGGAAAAGA TGTTTCATGG GGCCCAGACA
801  CGTTCTAG
```

Fig. 3B

| Fig. 3BI | Fig. 3B2 |
|---|---|

Fig. 3BI

E-box homology

```
                    E 2/3spacer(10/12)              (12/15)
                    ←
IgK3'    ACCTGCTCCCTACCCCAC CACCTGGC CAAGGCT
                          ←——→       →

IgH      CAGCTGGC AGGAAGCAGGT CATGTGGC-AAGGCT ATTTGGGGAAGG
         µE2  →    E 2/3spacer  →   µE3 →                  →

IgKIn    CAGGTGGC —— 42bp —— CATGTGGC
```

NF-κB homology

```
IgK3'        660    GGTTAGTCCCCAGTCCC
                    | |  ||||||||| | |
SV40                GGAAAGTCCCCAGGCTC        13/17
(invert)            ||||||||||
NF-κB               GGAAAGTCCCC
(invert)
```

IFN consensus

```
IgK3'        532    CTTTCAAGTTTCCAAAGC
                          |||||| ||||||
SV40                      AAGTTTGCAAAGC     12/13
                    |||||||  |||||
IFN                 CTTTCAA-TTTCC
(invert)

IgK3'        593    ATCCAGCACTGG
                     | ||||||||||
HLA-CUS             AATCAGCACTGG            10/12
(invert)
```

Fig. 3B2

LPV homology ———

```
Igκ3'   117   AGTATTTTCTACCTGGTAT
              ||| ||||||||||||||||
LPV a         AGTTTTTCTACCTGGTAT      17/18

Igκ3'   195   TCTGCAACAACA
              |  |||||||||
LPV b         TCTGCAAAAACA            11/12
```

Igκ intron homologies ├───┤

```
                    octa-like
Igκ3'   320   TATTGATTTTCAT
              |||||  |||||
IgκIn         TATTGTTTTTC             10/11

Igκ3'   379   AGTGTCCCATG
              | |||||||||
IgκIn         ATTGTCCATGTTGT          10/11
                      E3

Igκ3'   399   AGCAACTGTCA
              ||||||||| |
IgκIn         AGCAACTGCCAGATGGC       10/11
(invert)              E1
``` other SV40 homology ├── ── ──┤

```
Igκ3'   101   AATTGAGATTC
              ||||||||| |
SV40          AATTGAGATGC             10/11
```

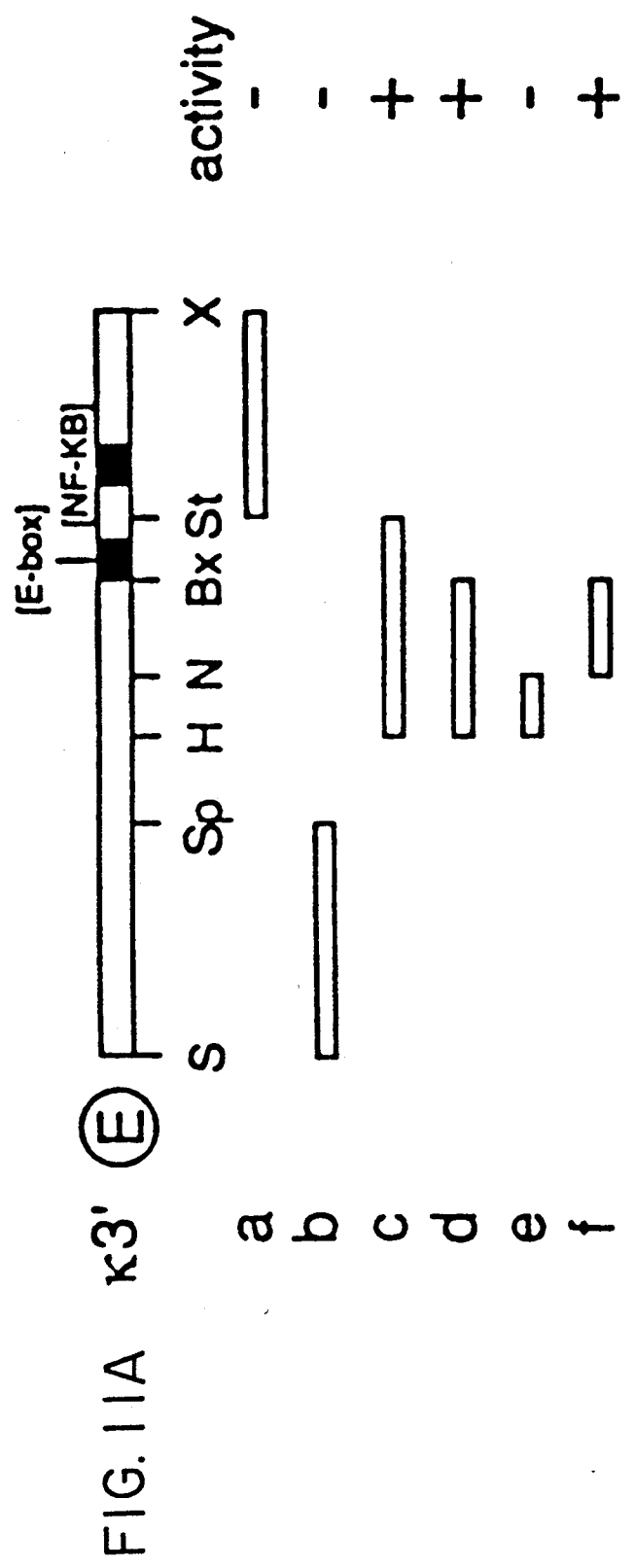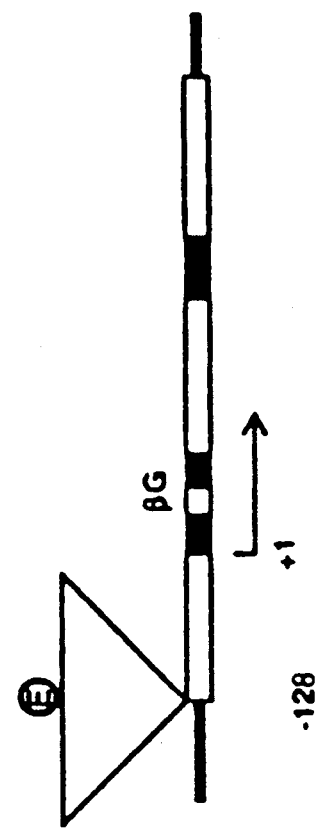
FIG. 11A
FIG. 11B a b c d e f SV—

β—

α—

FIG. 11C deletion:
2 3 4 5

| | Fig.14A |
|---|---|
| | Fig.14B |
| | Fig.14C |

Fig. 14A

| | POSITION NUMBER | | | | | | | | | |
|---|---|---|---|---|---|---|---|---|---|---|
| | 29 | 31 | 34 | 36 | 45 | 49 | 51 | 52 | 60 | 85 | 95 |
| V$_K$ Ox-1 | S | S | H | Y | K | Y | T | S | A | T | P |
| | AGT.. | AGT.. | CAC.. | TAC.. | AAA.. | TAT.. | ACA | TCC.. | GCT.. | ACT.. | CCA |
| NQT3 | | | | | | | | | | | |
| C13.1 | --- | --- | N<br>A-- | --- | --- | --- | --- | F<br>-T- | --- | --- | --- |
| F21.3 | --- | --- | N<br>A-- | F<br>-T- | --- | F<br>-T- | --- | --- | --- | --- | -G |
| G7.3 | --- | --- | --- | F<br>-T- | --- | --- | -T | --- | --- | --- | --- |
| H15.6 | --- | --- | --- | --- | T<br>-C | --- | --- | --- | --- | I<br>-T- | -G |
| NQT8 | | | | | | | | | | | |
| E10.1 | G--- | G | --- | F<br>-T- | --- | --- | --- | --- | S<br>T-- | --- | --- |
| L20.4 | G--- | G--- | N<br>A-- | --- | --- | --- | --- | --- | --- | --- | -G |

Fig. 14B

| | POSITION NUMBER | | | | | | | | |
|---|---|---|---|---|---|---|---|---|---|
| | 11 | 22 | 31 | 33 | 46 | 49 | 53 | 56 | 58 |
| | L | C | S | G | E | G | A | N | N |
| $V_H$ Ox-1 | CTG.. | TGC.. | AGC.. | GGT.. | GAG.. | GGA.. | GCT.. | AGC.. | AAT |
| NQT3 | | | | A | | | T | N | I |
| C13.1 | --- | --T | -C- | -C- | --- | --- | A-- | -A- | -T |
| F21.3 | --- | --- | -3- | --- | --A | --C | --- | --- | --- |
| G7.3 | --- | --- | T | --- | --- | --- | --- | --- | --- |
| H15.6 | --- | --- | -C- | --- | --- | --- | --- | --- | --- |
| NQT8 | | | T | | | | | | |
| E10.1 | --- | --- | -C- | --- | --- | --- | --- | --- | --- |
| L20.4 | --A | --- | T -C- | --- | --- | --- | --- | --- | --- |

Fig. 14C

| POSITION NUMBER | 59 Y TAT | 65 S TCC | 67 L CTG | 69 I ATC | 77 N AAC | 78 V GTT | 82C L CTG | 84 T ACT | 86 D GAC | 90 Y TAC | 91 Y TAC |
|---|---|---|---|---|---|---|---|---|---|---|---|
|  | F –TC | P C–– | – | – | – | – | – | – | – | – | – |
|  | – | – | T–– | – | –T | – | – | – | – | –T | – |
|  | – | – | – | – | S –G– | – | – | – | – | – | H C–– |
|  | – | – | – | – | – | – | – | – | – | – | – |
|  | – | – | – | –A | – | L C–– | – | – | – | – | – |
|  | – | – | – | – | – | – | –C | N –A– | – | – | – |
|  | – | – | – | – | – | – | – | – | –T | – | – |

Fig. 15A

```
                        V REGION   [350bp]
                         2   11  30  36  33  49  51  68  74  76  90  96  103
                         I   M   V   Y   Q   Y   N   G   T   S   Q   L   K
TRANSGENE               ATT.ATG.GTA.TAC.ATG.TAT.ACA.GGG.ACA.AGC.CAG.CTC.AAG
 SEQUENCE
LINE      cDNA
HYBRIDOMA CLONE Noe
kOx²
NQT3/C13.1  1
            2 to 7      ---.---.---.---.G--.---.---.---.---.---.---.---.---
            8 to 16     ---.---.---.---.---.---.---.---.---.---.---.---.---

NQT3/F21.3  1           ---.---.---.---.---.-T-.---.---.---.---.---.---.---
            2           ---.---.---.---.---.---.---.---.-G-.---.---.---.---
            3           ---.---.---.---.---.---.---.---.---.--G.--A.---.---
            4           ---.---.---.---.---.---.---.---.---.---.---.---.-T-
           11 to 20     ---.---.---.---.---.---.---.---.---.---.---.---.---
            6           ---.---.---.---.---.---.---.---.---.---.---.---.---
            7 to 16     ---.---.---.---.---.---.---.---.---.---.---.---.---

NQT3/G7.3   1           ---.---.---.---.---.---.---.-A-.---.---.---.---.---
            2           ---.---.---.---.---.---.---.---.---.---.---.---.---
            3 to 10     ---.---.---.---.---.---.---.---.---.---.---.---.---
           11 to 20     ---.---.---.---.---.---.---.---.---.---.---.---.---

NQT3/H15.6  1           -C-.---.---.---.---.---.---.---.---.---.---.---.---
            2           ---.---.---.---.---.---.---.---.---.---.---.---.---
            3           ---.---.---.---.---.---.---.---.---.---.---.-T-.---
            4 to 19     ---.---.---.---.---.---.---.---.---.---.---.---.---
```

```
kOx⁴
NQT8/E10.1    1         ---   --- -C- --- --- --- ---   --- --- --- --- --- --- ---
              2         ---   --- --- --- --- -G- ---   --- --- --- --- --- --- ---
              3         ---   --- --- -G- --- --- ---   --- --- --- --- --- --- ---
              4         ---   --- --- --- --- --- ---   --- --- --- --- --- --- ---
              5         ---   --- --- --- --- --- ---   --- --- --- --- --- --- ---
              6 to 11   ---   --- --- --- --- --- ---   --- --- --- --- --- --- ---
              12 to 30  ---   --- --- --- --- --- ---   --- --- --- --- --- --- ---

NQT8/L1.10    1         ---   --- --- --- --- --- ---   --- --- --- --- --- --- ---
              2         ---   --- --- --- --- --- ---   --- --- --- --- --- --- ---
              3 to 10   ---   --- --- --- --- --- ---   --- --- --- --- --- --- ---

NQT8/L20.4    1         ---   --- --- --- --- --- C--   --- --- --- --- --- --- ---
              2 to 20   ---   --- --- --- --- --- ---   --- --- --- --- --- --- ---
```

TOTAL NUMBER OF CHANGES V REGION : 13 CHANGES IN 48 kb

*Fig. 15B*

| *Fig. 15A* | *Fig. 15C* |
|---|---|
| *Fig. 15B* | *Fig. 15D* |

```
            C REGION      [270bp]
109 130 139 142 143 146 150 162 164 169 188 189
 A   A   F   R   D   V   I   S   T   K   H   K
GCT.GCC.TTC.AGA.GAC.GTC.ATT.AGT.ACT.AAA.CAT.AAG

C REGION : 13 CHANGES IN 22 kb

Fig. 16

| Fig.16A | Fig.16B |
|---------|---------|

Fig. 16A

| Amino Acid | 9<br>A<br>GCA | 10<br>I<br>ATC | 14<br>S<br>TCT | 26<br>S<br>AGC | 31<br>S<br>AGT | 33<br>M<br>ATG | 36<br>Y<br>TAC | 39<br>K<br>AAG |
|---|---|---|---|---|---|---|---|---|
| HYBRIDOMA | cDNA CLONE # | | | | | | | |
| NQT15/12 1,2,3,8,<br>6,7,9,10 | --- | --- | --- | --- | --- | --- | --- | --- |
| 4 | --- | --- | --- | --- | -A- | --- | --- | --- |
| NQT15/17 1 | -T- | --T | --- | -A- | --- | --- | --- | --- |
| 2 | -T- | --T | -T- | -A- | --- | --- | --- | --- |
| 3,4 | -T- | --- | --- | -A- | --- | --- | --- | --- |
| 5,9 | --- | --- | --- | --- | --- | --- | --- | --- |
| 6,7,8 | --- | --T | --- | -A- | -A- | -C- | -T- | --- |
| 10 | -T- | --- | --- | --- | --- | --- | --- | --- |
| NQT15/20 1,2,3,4,6,7,9,10<br>5,8 | --- | --- | --- | --- | --- | --- | --- | --- |

Fig. 16B

ENHANCERS

FIELD OF INVENTION

This invention relates to enhancers and concerns recombinant DNA molecules comprising a novel enhancer, and use of the enhancer in gene expression and gene therapy.

BACKGROUND OF THE INVENTION

Enhancers are DNA sequences which play an important role in the transcription of proteins. A number of different enhancer sequences have been identified from different sources, including enhancers of vital origin, e.g. from the SV40 virus, and of cellular origin. As regards the immunoglobulin (Ig) genes, enhancer elements have been identified in the major introns of both the heavy chain (IgH) (Banerji et al., 1983; Gillies et al., 1983; Neuberger, 1983) and kappa (identified herein as "K") light chain (Picard and Schaffner, 1984; Queen and Stafford, 1984) loci.

The present invention is based on the identification of a novel enhancer in the mouse immunoglobulin K locus, downstream of $C_K$, in addition to the K-intron enhancer. Functionally equivalent enhancers are to be expected to occur downstrem of $C_K$ of the immunoglobin K locus of other species.

SUMMARY OF THE INVENTION

According to one aspect of the present invention there is provided a recombinant DNA molecule comprising an enhancer having at least part or parts of the base sequence occuring downstream of $C_K$ of the immunoglobulin K locus of any species.

The enhancer located in the mouse K locus occurs in the sequence given in FIG. 3A, and the location of the enhancer has been further localised to the sequence given in FIG. 12B.

Thus, in a further aspect the invention provides a recombinant DNA molcule comprising an enhancer having at least part or parts of the following base sequence:

AGAAGACCCTTTGAGGAACT-
GAAAACAGAACCTTAGG-
CACATCTGTTGC

In another aspect the invention provides a recombinant DNA molecule comprising an enhancer having at least part or parts of the base sequence given in FIG. 3A.

The following refers generally to work on the enhancer located in the mouse K locus. It will be apparent to those skilled in the art that functionally equivalent enhancers in other species can be identified by routine investigation.

The novel enhancer is located about 9 kb downstream (3') of $C_K$, and is known as the K3'-enhancer. Like the K-intron enhancer, the K3'-enhancer is also B cell specific. This novel enhancer is some sevenfold stronger than the K-intron enhancer and the region of the enhancer shows striking sequence homologies to the lymphotropic papovavirus, IgH and K-intron enhancers. The location of the K3'-enhancer between $C_K$ and the RS element means that it is likely to be deleted, at least one allele, in many B cells that express lambda light chains.

The existence of a second enhancer in the mouse K locus explains various previously unexplained observations. For example, locus, transgenes containing all the previously identified K transcription elements were not expressed at high level (Rusconi and Kohler, 1985; Pettersson et al., 1989). Furthermore, the endogenous K gene in the S107 plasmacytoma cell line is well expressed despite the fact that the intron-enhancer is not active in this cell line, which lacks the enhancer binding factor NF-KB (Atchinson and Perry, 1987,1988). The existence of multiple activating sequences in the region of the immunoglobulin loci may also explain why many immunoglobulin transgenes are less transcriptionally active than the endogenous loci; the transgenes may not include the full complement of activating sequences. Indeed, we have found only weak transcriptional activity in transgenic mice that harbour a K transgene that extends only 1.2 kb downstream of the $C_K$ exon.

The molecule of the invention may additionally comprise other elements, and will generally further comprise a promoter and gene or genes coding for a protein or proteins of interest. One or more additional enhancers may also be included.

The novel enhancer may be used in any geometrical configuration of DNA arrangement. The enhancer is preferably closer to a promoter than the natural spacing (in a functionally rearranged K gene the enhancer is about 3 kb downstream of the promoter), as this is found to give improved levels of gene expression. Expression levels may also be improved by locating the enhancer close to the protein coding region.

The role of the K3'-enhancer in K gene expression has keen examined, and experiments with transgenic mice have shown that the region including the 3'-enhancer is necessary to achieve, and enables achievement of, high level expression of K transgenes. Its omission leads to poor allelic exclusion and a 20–50 fold lower level of K synthesis. Transfection experiments reveal that the 3'-enhancer also acts to give a significant increase in the expression of K genes introduced into cell lines. Deletion mapping of the enhancer localises its activity to a 50 nucleotide region that lacks an NF-KB site: indeed the 3'-enhancer allows K expression in a cell in which lacks NF-KB. Thus this enhancer is necessary for proper K light chain expression and is induced by a pathway distinct from that used for the intron-enhancer, which is dependent on NF-KB.

The novel enhancer may thus be used to enhance expression of genes in host cells, in vivo and in vitro, particularly in certain lymphoid cell lines and in transgenic animals.

Because the inclusion of the 3'-enhancer in K transgenes dramatically improved the expression of such transgenes, this has important implications for the use of transgenic animals for the production of large amounts of antibody which is encoded by the transgene or for producing a repertoire of human monoclonal antibodies. Further, experiments have shown that the high expression of the transgene also means that expression of endogenous light. chain genes is minimised: this fact could also be of use in making a transgenic animal which mainly makes transgenically-encoded antibody.

Work has also been carried out to investigate the role of the novel enhancer in somatic mutation of antibody genes in transgenic mice.

The antigen-binding site of an antibody is formed by the combination of the variable domains of the antibody heavy and light chain. These variable domains are in turn encoded by a combination of gene segments:

$V_H$, $D_H$ and $J_H$ for the heavy-chain and $V_L$ and $J_L$ for the light chain. There are several such segments in the genome. However, a particular antibody-producing B lymphocyte uses a particular combination of V, D and J segments and this ability to choose different combinations contributes to the diversity of the antibody repertoire that an animal can make (combinatorial diversity). However, there is another diversity imposed on top of this due to somatic mutation. A B lymphocyte is able to introduce mutations into the particular rearranged antibody genes that it harbours. In other words, having chosen a specific $V_H D_H J_H / V_L J_L$ combination, a B cell can (at a later stage) specifically target mutations to these rearranged gene segments. Thus, when the mouse is first immunised, the antigen binds to specific B cells which happen to carry antibodies which have a variable domain which binds the antigen. These B cells now go on to secrete the cognate antibody. However, these activated B cells can also now target a somatic mutation process to their rearranged antibody gene segments and thus allow the production of daughter cells which make variants of the antibodies of the primary response. A selection process now amplifies those variant B cell descendants which make an antibody of improved affinity of the antigen. Thus somatic mutation allows affinity maturation—the production and selection of high affinity antibodies. Therefore, somatic mutation is important for the generation of high affinity antibodies.

The work has demonstrated that transgenes which contain the region downstream of $C_K$ which includes the 3'-enhancer can be somatically mutated; shorter transgenes cannot. Thus, if one is creating a transgenic animal for the purpose of making a repertoire of high affinity human antibodies, it is important that the region spanning the 3'-enhancer be included in the transgene. On the other hand, if the purpose is to make an animal which makes a specific, unique transgenically-encoded antibody, it may be desirable to ensure that the transgene cannot be a target for the somatic mutation process and therefore to avoid the 3'-enhancer.

Because the novel enhancer is B cell specific it may be used to target tissue specific expression of genes. This property means the enhancer potentially finds particular use in certain therapeutic applications, for targeting production of proteins, and in hybridoma technology.

The sequence of the novel enhancer may be derived by recombinant DNA techniques from a naturally occurring gene system or may correspond to a naturally occurring gene system in the sense of being manufactured using known techniques of polynucleotide synthesis from sequence data relating to a naturally occurring gene system. Alterations of the sequence may be made which do not alter the function of the enhancer.

The invention also provides a vector for the integration of a gene into the genetic material of a host cell such that the gene may be expressed by the host cell, the vector comprising the gene, a promoter and the novel enhancer.

The term "vector" as used herein connotes in its broadest sense any recombinant DNA material capable of transferring DNA from one cell to another.

The vector may be a single piece of DNA in linear or circular form and may additionally include such other sequences as are necessary for particular applications. For example, the vector may contain additional features such as a selectable marker gene or genes, and/or features which assist translation or other aspects of the production of a cloned product.

The term "gene" as used herein connotes a DNA sequence, preferably a structural gene encoding a polypeptide. The polypeptide may be a commercially useful polypeptide, such as a pharmaceutical and may be entirely heterologous to the host cell. Alternatively the gene may encode a polypeptide which is deficient, absent or mutated in the host cell.

The host cell may be any host cell susceptible to uptake of the vector of the invention. The vector DNA may be transferred to the host cell by transfection, infection, microinjection, cell fusion, or protoplast fusion.

The host cell may be a cell of living human or animal. In particular, the host cell may be a cell of a transgenic animal such as a mouse. The host cell may be a human stem cell such as bone marrow cell.

The promoter may be any promoter capable of functioning in the host cell and may be for example a mammalian or vital promoter.

The invention also includes within its scope a host cell, e.g. of a cell line or a transgenic animal, transformed with a molecule or vector according to the invention.

The invention further provides a method of producing a polypeptide, comprising culturing a host cell transformed with a molecule or vector according to the invention.

The method may be applied in vitro to produce a desired polypeptide. In addition, the method may be applied in vivo to produce a polypeptide having no therapeutic value to the animal. Such a method of producing a polypeptide is not to be considered as a method of treating the human or animal body.

In a further aspect of the invention the vector or molecule may be used in a method of treatment of the human or animal body by replacing or supplementing a defective gene.

Many diseases of the human or animal body result from deficiencies in the production of certain gene products. The characterising features of the vectors of this invention make them amply suited to the treatment of deficiencies by gene therapy in vivo.

A method of gene therapy is thus provided comprising removing stem cells from the body of a human or an animal, killing stem cells remaining in the body, transforming the removed stem cells with a vector or molecule of the invention containing a gene deficient, or absent, in the human or animal body, and replacing the transformed stem cells in the human or animal body. This method can be used to replace or supplement a gene deficient in a human or animal.

Bone marrow is a suitable source of stem cells and is advantageous in that it contains the precursors of both lymphocytes and erythroid cells. Alternatively other tissue could be removed from the body transfected or otherwise provided with a vector or molecule of the invention and implanted back into the body.

The invention will be further described, by way of illustration, with reference to the accompanying Figures, in which.

Figure 1A:
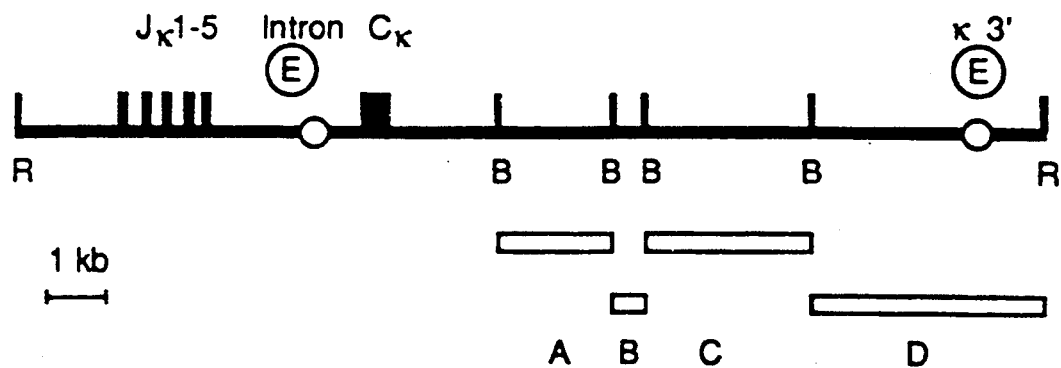
FIG. 1A is a map of the mouse K locus depicting the fragments A to D assayed for enhancer activity.
Figure 1B:
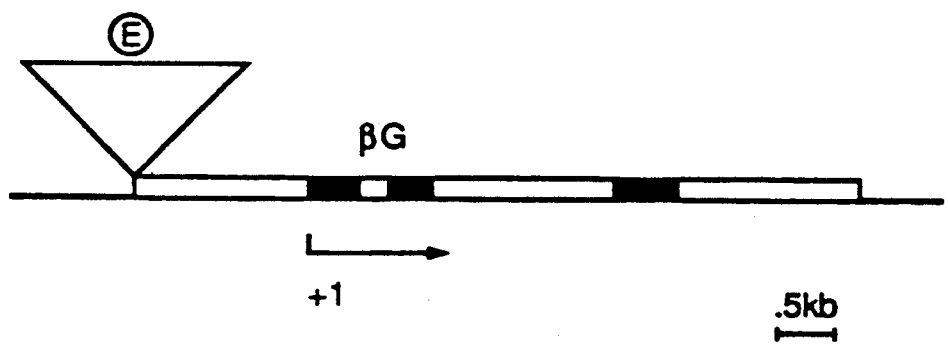
FIG. 1B is a schematic representation of the pbeta800 plasmid used for enhancer assays.

FIG. 3A (consisting of FIGS. 3A1 and 3A2) illustrates the base sequence of the SacI-XbaI enhancer fragment identified in FIG. 2 and containing the novel K3' enhancer; (Sequence listed as SEQ. ID NO:2--; and Neuberger M. No. 07/768,437.

Figure 4:
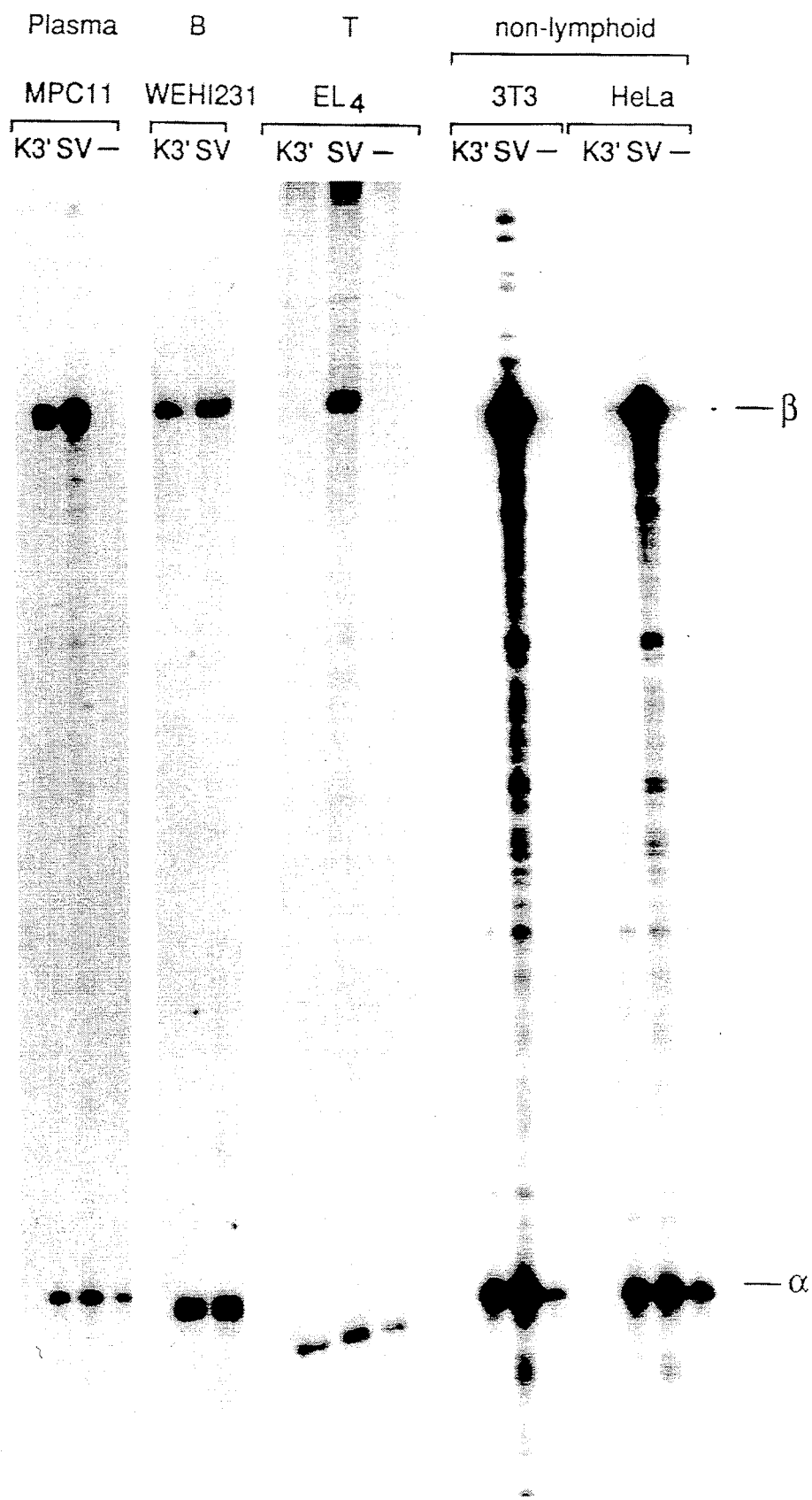
Figure 5A:
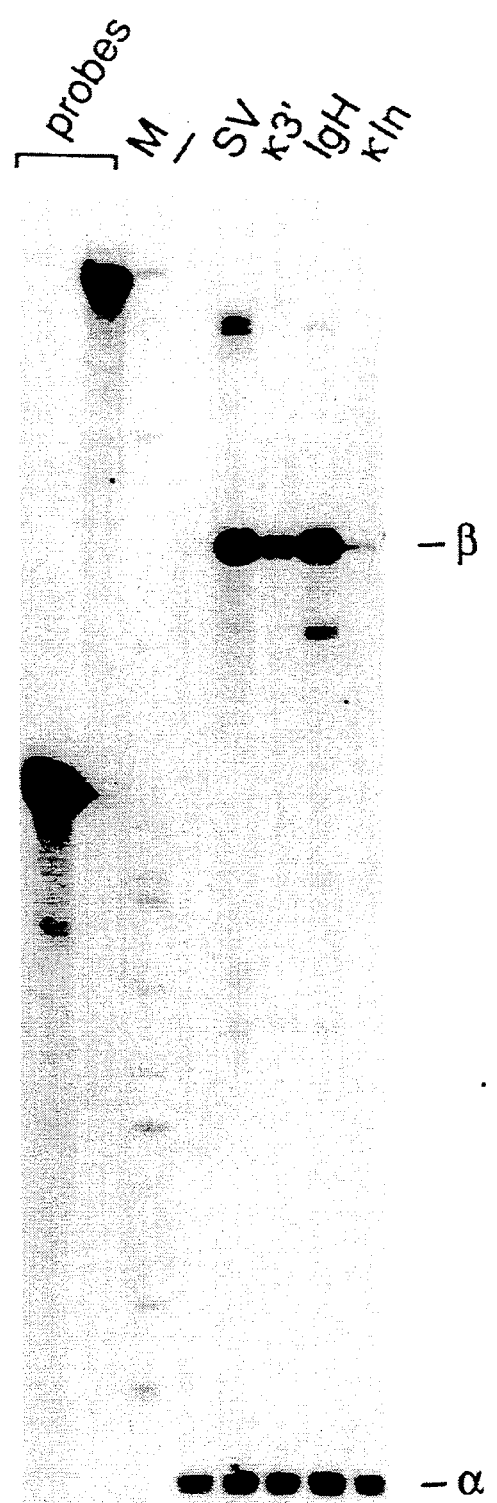
Figure 5B:
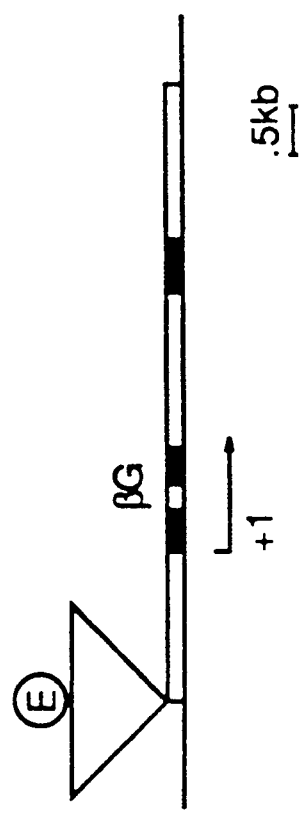
Figure 6A:
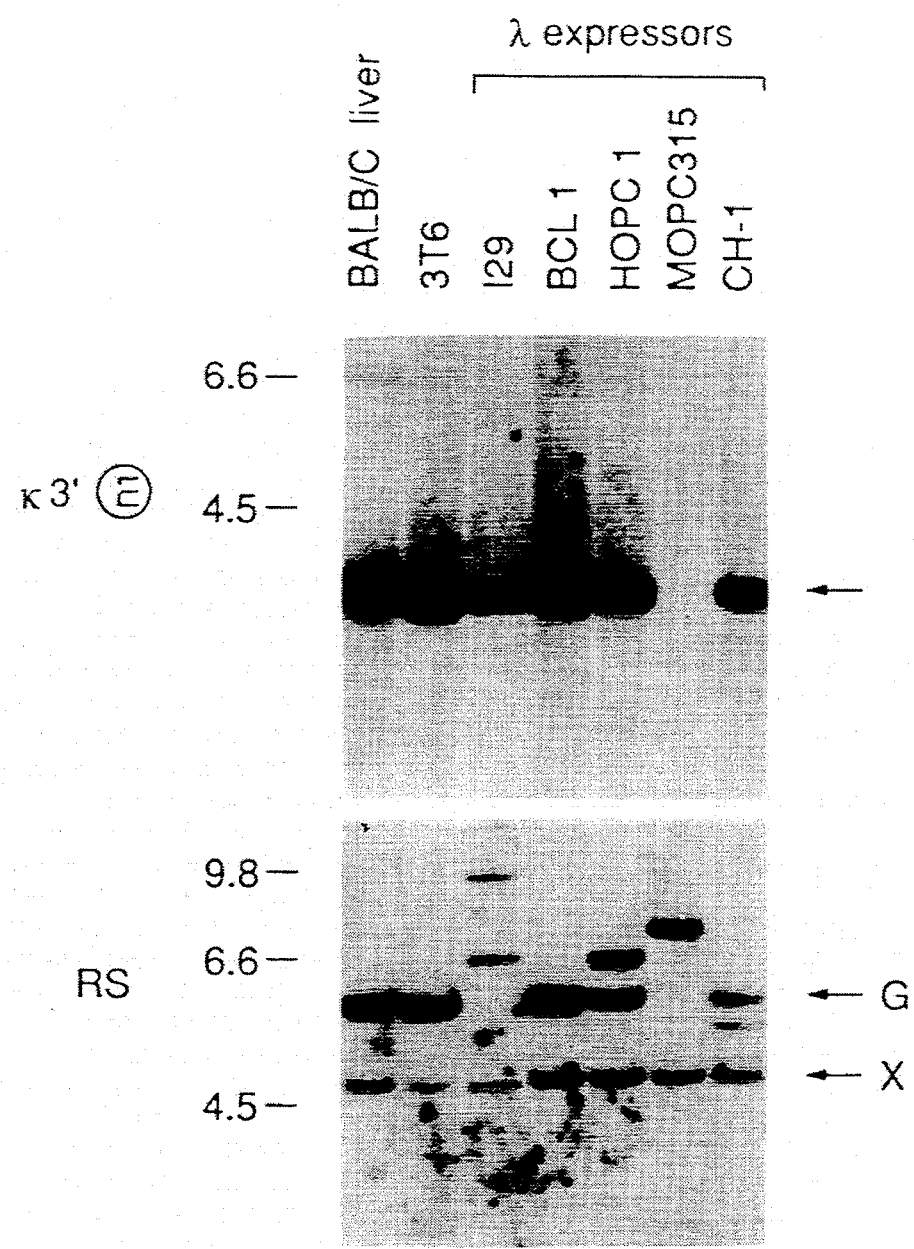
Figure 6B:
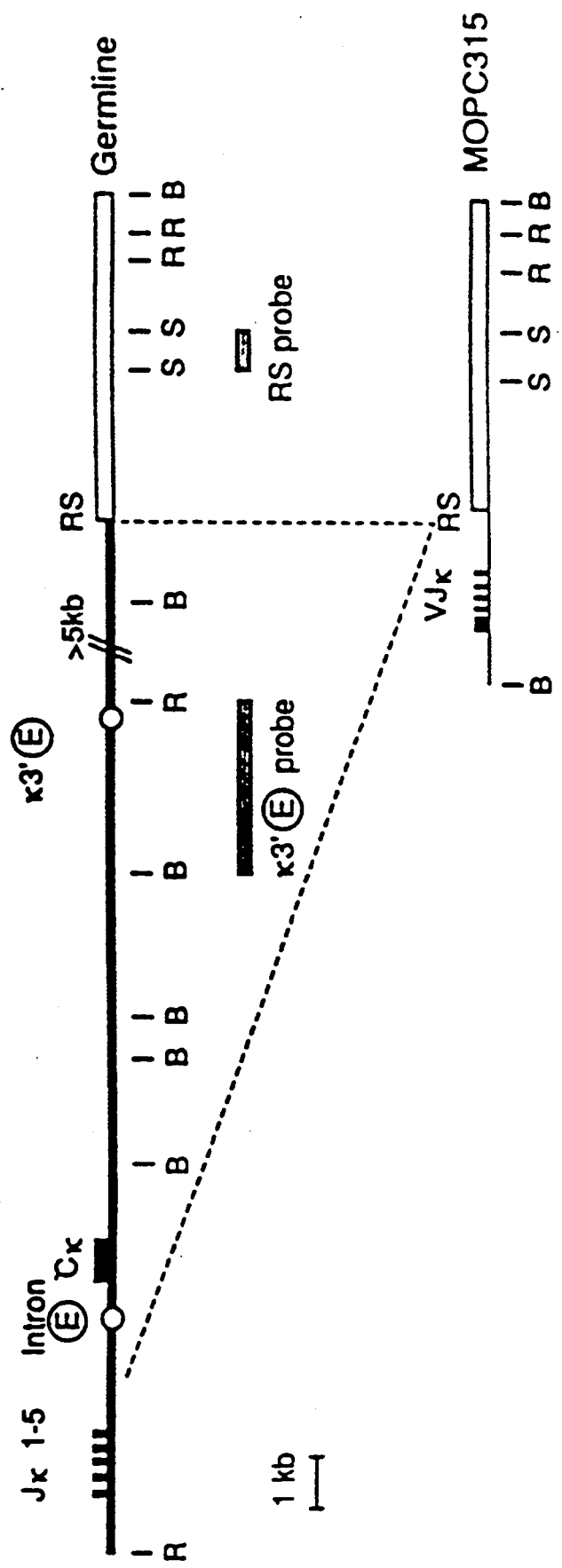
Figure 7:
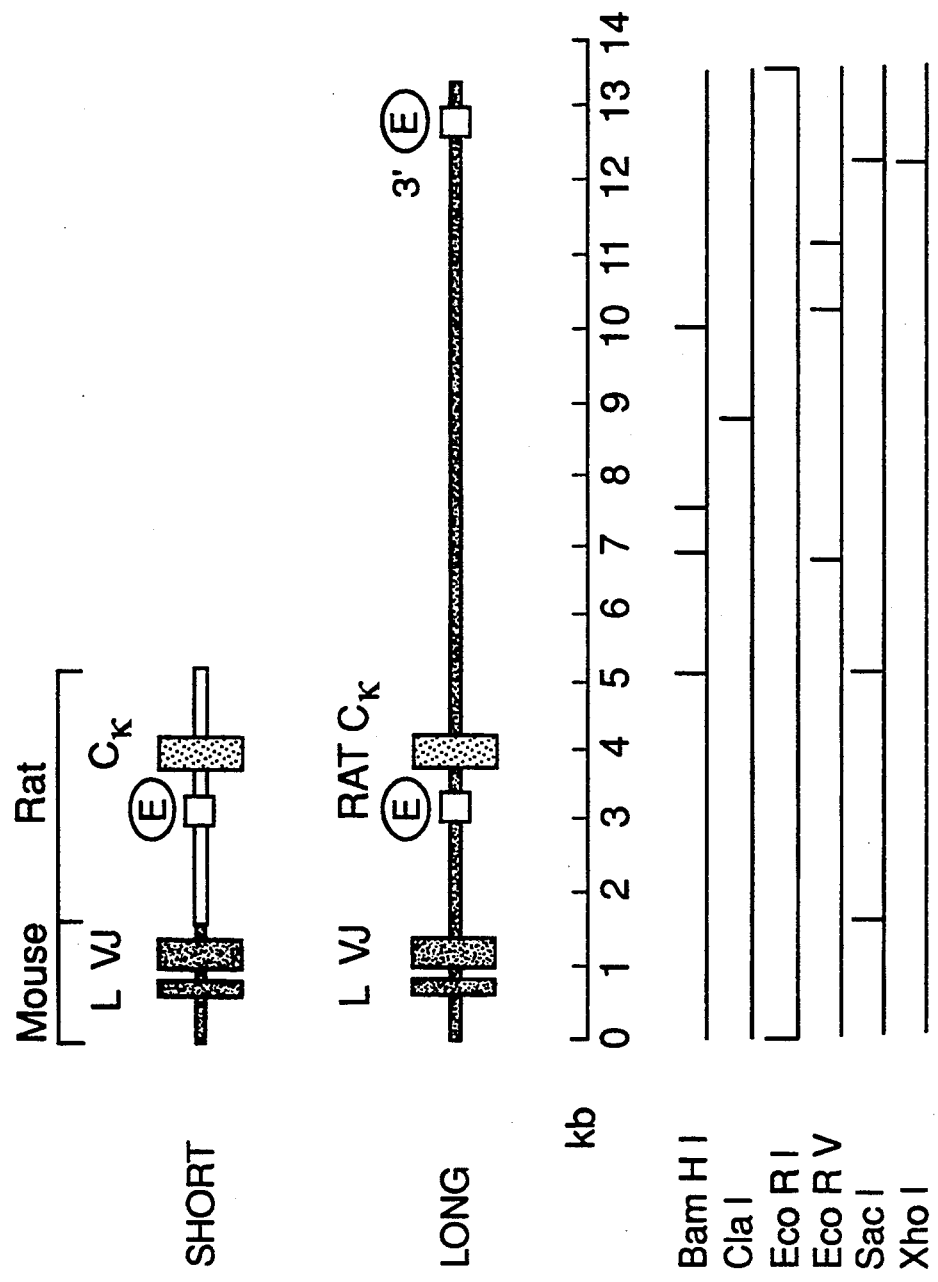
Figure 8:
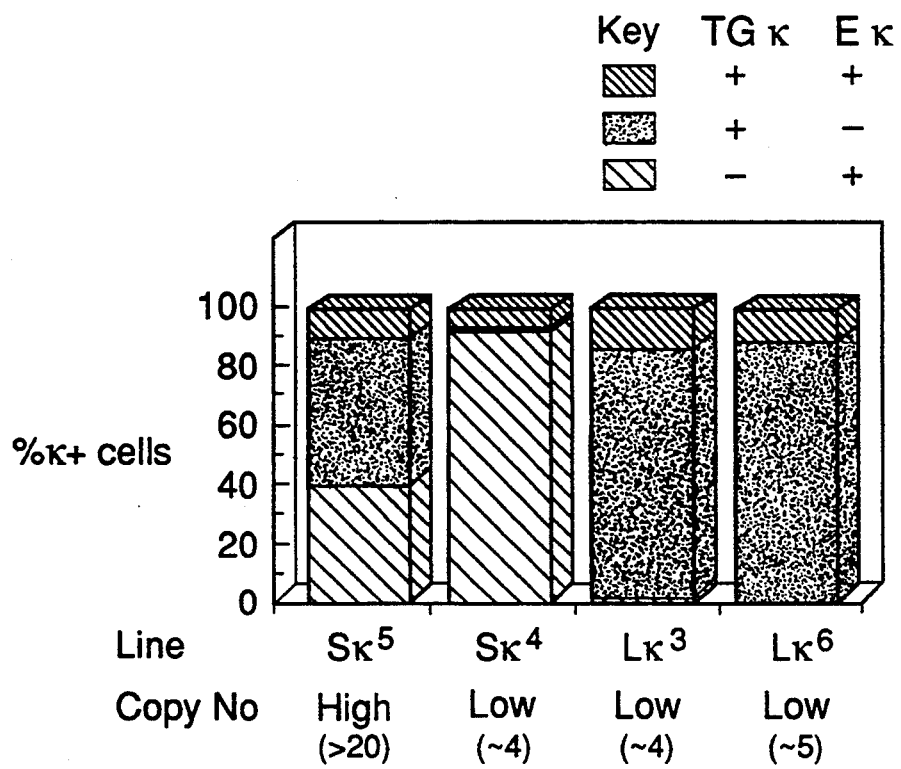
Figure 9:
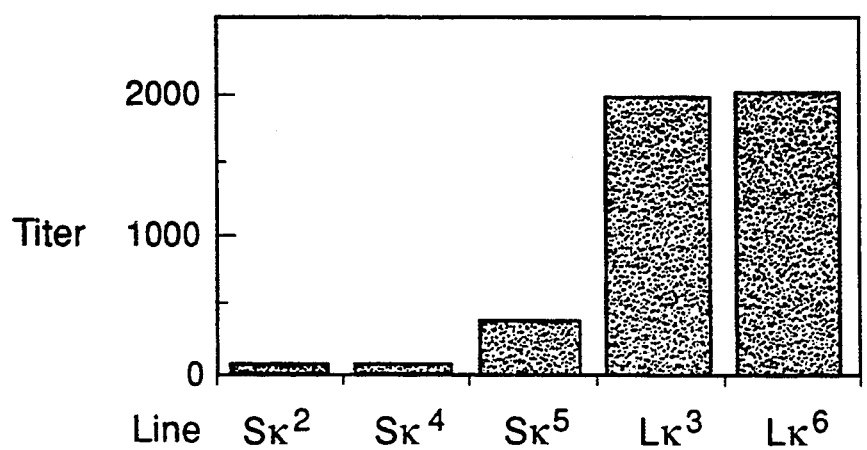
Figure 10A:
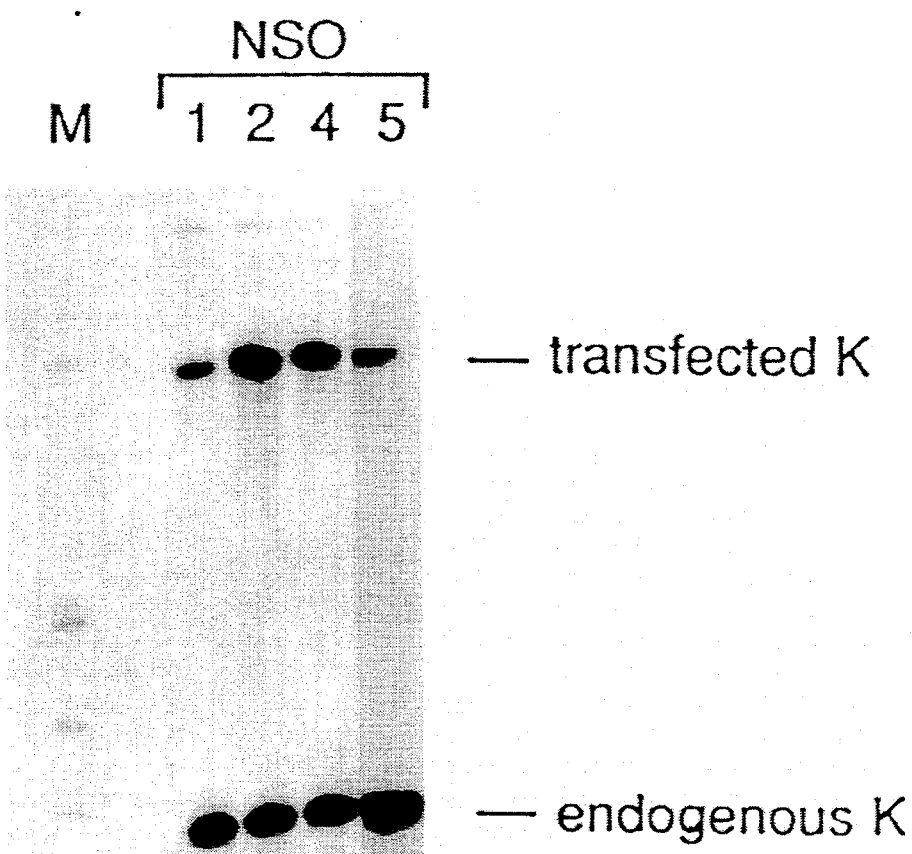
Figure 12B:
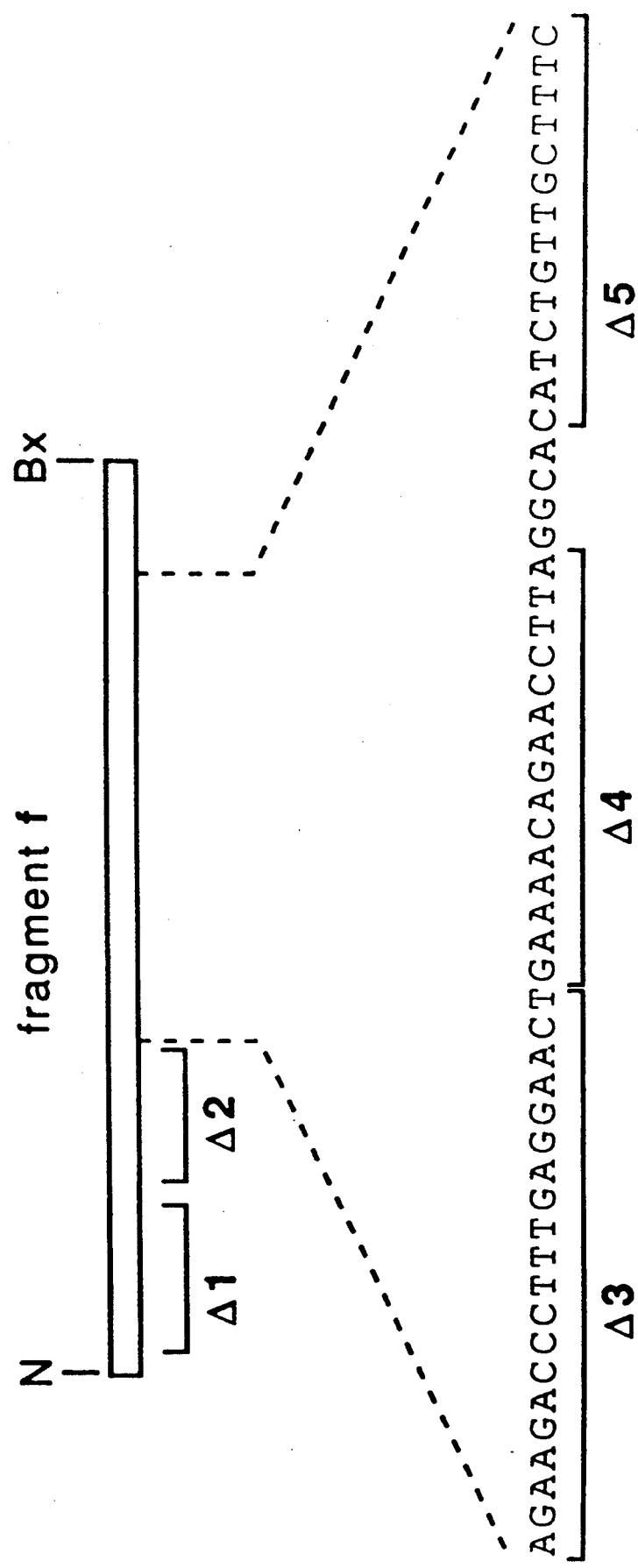
Figure 13A:
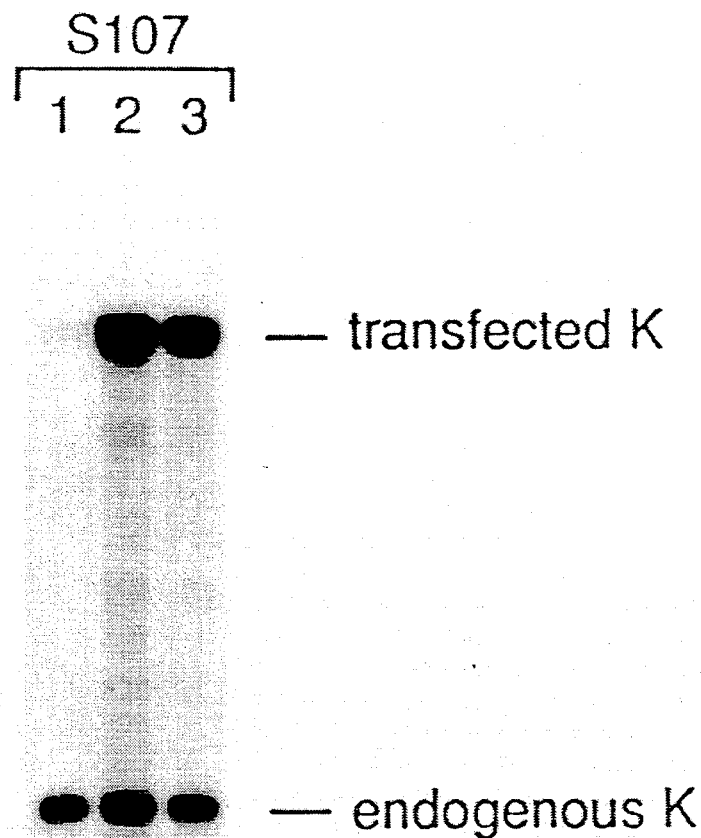
Figure 13B:
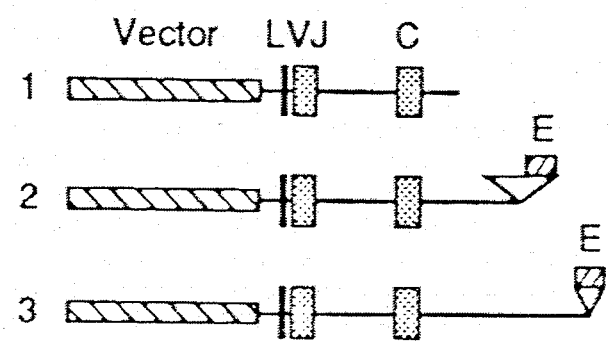

FIG. 3B (consisting of FIGS. 3B1 and 3B2) indicates sequence homologies, with boxes and lines being used to identify homologies in FIGS. 3A and 3B Individual SEQ ID NO: 4 to SEQ ID NO: 13 are shown in the left column wherein SEQ ID NO: 5 and SEQ NO: 6 list the sequences 5' and 3' respective of the gap in the sequence IgH. SEQ ID NO: 14 to SEQ ID NO: 25 are shown in the right column;

FIG. 4 illustrates cell-type specificity of the K3' enhancer;

FIG. 5A illustrates the results of ribonuclease protection assays to compare activity of the K3' enhancer FIG. 5B is an illustration of a beta-globin plasmid; and the K-intron enhancer;

FIG. 6A is a Southern blot of various lambda-expressing cell lines;

FIG. 6B is a map of the mouse K locus showing the RS element as well as the rearranged RS allele of plasmacytoma MOPC315;

FIG. 7 illustrates long and short K gene constructs used to establish transgenic mouse lines;

FIG. 8 shows histograms illustrating immunofluorescence analysis of K gene expression in transgenic mice;

FIG. 9 illustrates titration of transgenic light chain secreted by of hybridomas from the transgenic mice;

FIGS. 10A, B and C illustrate expression of K genes transfected into NSO;

FIGS. 11A, B and C illustrate future delimitation of enhancer activity, with FIG. 11A being a map showing the subfragments of the 808bp SacI-XbaI K3'-enhancer that were assayed for activity; FIG. 11B being a schematic representation of plasmid pbeta128 used for the enhancer assays; and FIG. 11C illustrating the result of a ribonuclease protection assay;

FIGS. 12A and B illustrate functional deletional analysis of enhancer subfragment f of FIG. 11A, with FIG. 12A illustrating the results of ribonuclease protection assays using deletions illustrated in FIG. 12B (FIG. 12B illustrates SEQ ID NO:3);

FIG. 13A illustrates the results of ribonuclease protection assay of K transcription in 3 stable transfectants of plasmacytoma S107, illustrated in FIG. 13B, showing that the 3' enhancer allows expression of transfected K genes in S107;

FIG. 14 (consisting of FIGS. 14A, 14B and 14C) illustrates point mutations in the endogenous V region sequences of anti-phOX hybridomas from transgene mice, with FIG. 14A giving details for the oxazolone light chain V regions and FIGS. 14B and 14C giving details for the oxazolone heavy chain V regions;

FIG. 15 (consisting of FIGS. 15A, 15B, 15C and 15D) illustrates nucleotide changes in transgene cDNA clones from anti-phOX hybridomas from transgenic mice; and FIG. 16 (consisting of FIGS. 16A and 16B) illustrates nucleotide changes in transgene cDNA clones from anti-phOX hybridomas from transgenic mice.

DETAILED DESCRIPTION

An Enhancer is Located 9 kb Downstream of $C_K$

Experiments were carried out to look for a second enhancer implicated in K gene transcription, located 3' of the $J_K$ segments. The germline $V_K$ genes, at least in man, are scattered over some several thousand kb upstream of $J_K$; much of the DNA upstream of $J_K$ is deleted in K expressing cell-lines (Klobeck et al., 1987). To test for enhancer activity downstream of $C_K$, we exploited the fact that the human beta-globin gene in plasmid pbeta800 (FIG. 1B) is only a weak transcription unit in transfected cells unless it is provided with an exogenous enhancer element. Various DNA fragments from the germline mouse K clone L1 (Steinmetz et al., 1979) shown in FIG. 1A were assayed for enhancer activity. In this Figure the two K enhancers (K-intron E and K3'E) are indicated and restriction sites are abbreviated as follows: B, BamHI; R, EcORI. The BamHI fragments A to D of FIG. 1A and also the SV40 enhancer (SV) (for comparative purposes) were subcloned into plasmid pbetaG800 (FIG. 1B), with the fragments being placed 800 bp upstream of the beta-globin start site. The DNA from the resulting constructs, and also from pbetaG800 containing no enhancer (—) for comparative purposes, was introduced into MPC11 myeloma cells by calcium phosphate coprecipitation along with a human alpha 2-globin plasmid that provided an internal reference. The amount of beta- and alpha-globin mRNA produced by the transfected cells was then measured in ribonuclease protection assays, and the results are given in FIG. 1C. In this Figure bands corresponding to correctly initiated beta-globin transcripts are indicated as are the alpha-globin transcripts encoded by the co-transfected reference plasmid.

Figure 1C:
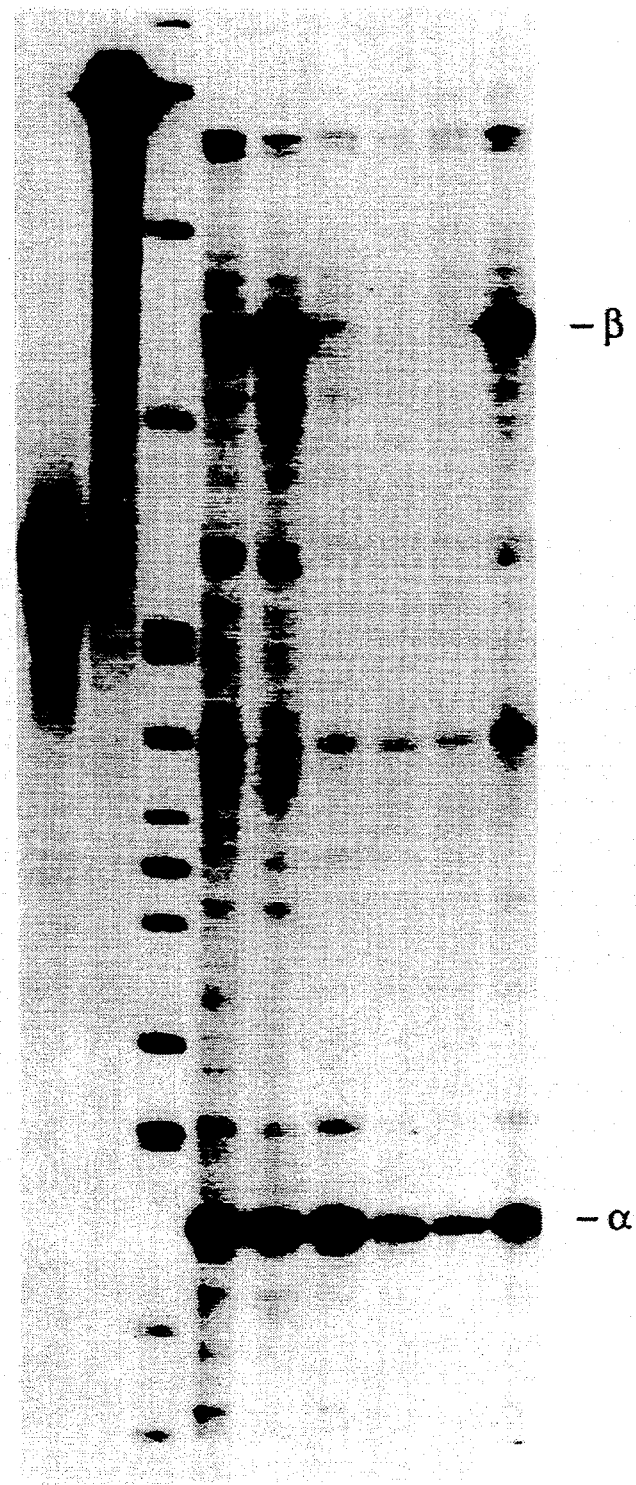
FIG. 1C illustrates ribonuclease protection assays of beta- and alpha-globin mRNA in MPC11 cells transfected with either pbeta800 (−) or with derivatives in which either the SV40 enhancer or one of fragments A to D have been cloned in at −800.

As can be seen from FIG. 1C, little mRNA is produced from the beta-globin gene in the absence of an exogenous enhancer; however, provision of the SV40 enhancer strongly activates transcription. As regards the DNA fragments from the K locus, strong stimulation of beta-globin transcription was found using fragment D but no such stimulation was found using fragments A, B or C. Thus, inclusion of fragment D on the plasmid but at a distance from the beta-globin gene activates transcription from the beta-globin promoter. The existence of a transcription enhancer element within fragment D is deduced, and this enhancer is referred to as the K3'-enhancer to distinguish it from the K-intron enhancer located in the $J_KC_K$ intron that has been identified previously (Queen and Baltimore, 1983; Picard and Schaffner, 1984; Queen and Stafford, 1984).

Figure 2A:
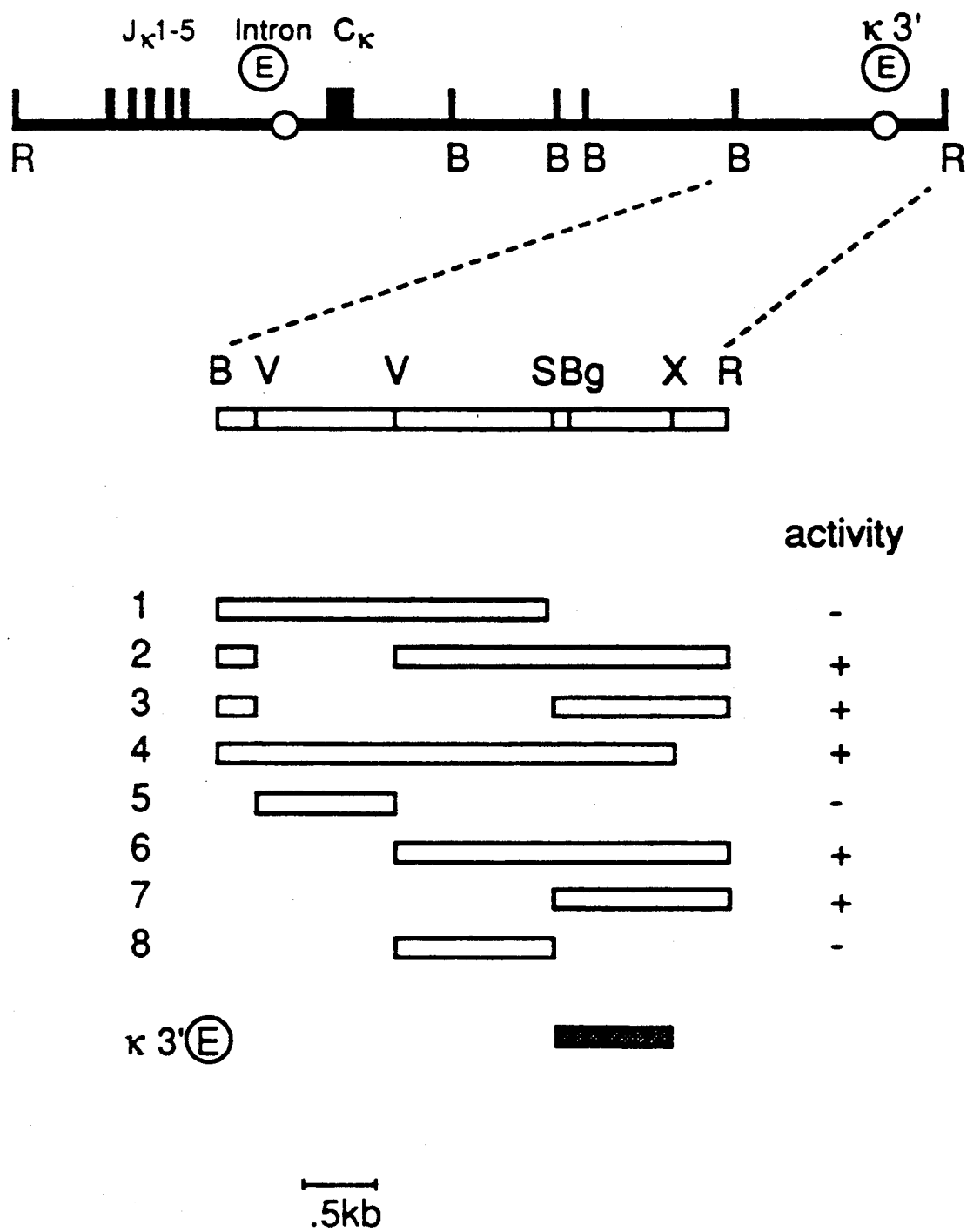
FIG. 2A is a map showing fragments of fragment D of FIG. 1A assayed for enhancer, activity.

To delineate the K3'-enhancer element further, assays were made of a number of deletions of fragment D (constructs 1-4 identified in FIG. 2A) as well as some individual subfragments (constructs 5-8 identified in FIG. 2A). In FIG. 2A, restriction sites are abbreviated as in FIG. 1A plus the following: Bg, BglII; S,SacI; V, EcoRV; X, XbaI. The bars depict the K locus included in each construct. MPC11 cells were transfected with the alpha 2-globin reference plasmid plus either plasmid pbeta800 containing no enhancer (—) or with derivatives that included at position —800 either the SV40 enhancer (SV) or the K DNA fragments 1 to 4 that are depicted in FIG. 2A. Lanes 5 to 8 were obtained by transfection with pbeta128 derivatives in which K DNA fragments were cloned into position −128. (The pbeta128 plasmid is identical to pbeta800 except that it includes 128 bp rather than 800 bp of beta-globin 5' flanking DNA.) The results are given in FIG. 2B, with the positions of correctly initiated alpha and beta-globin transcripts indicated.

Figure 2B:
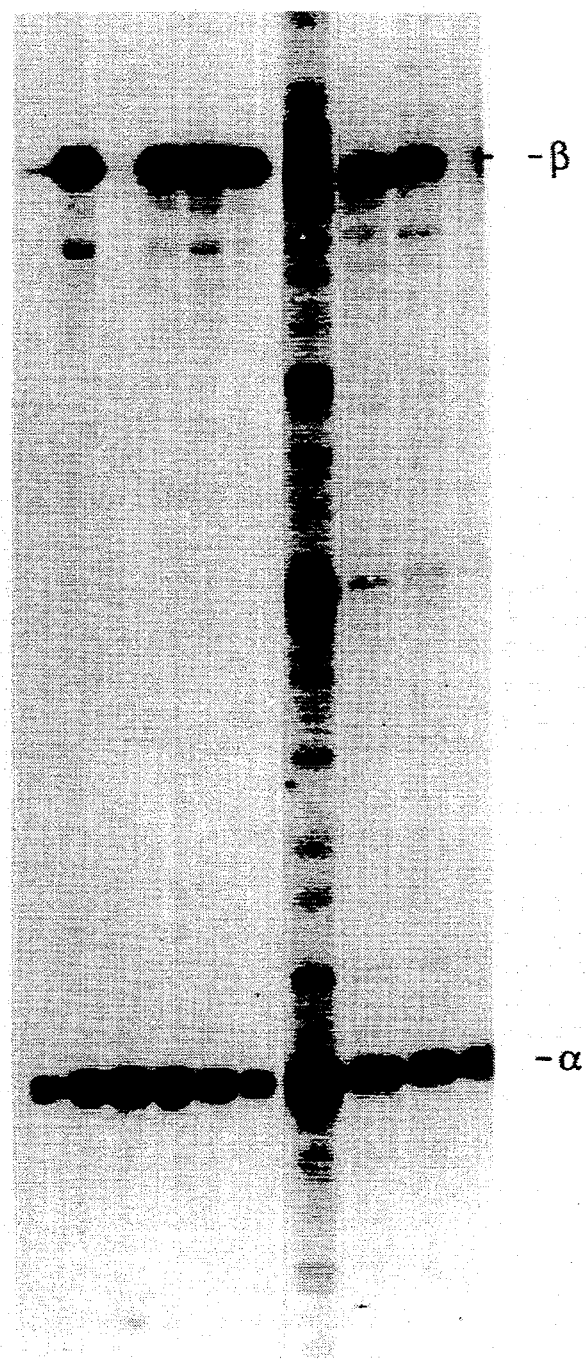
FIG. 2B illustrates the results of ribonuclease protection assay of enhancer activity.

As shown in FIG. 2B, enhancer activity was found in constructs 2, 3, 4, 6 and 7 but not in constructs 1, 5 and 8. This suggests that the enhancer is located within the 0.8 kb SacI-XbaI fragment, a prediction that was confirmed by subcloning this fragment into an enhancerless beta-globin vector (FIG. 4). The novel enhancer is located approximately 9kb downstream of $C_K$.

The K3'-Enhancer Contains Regions Homologous to the IgH, K-intron and LPV enhancers The sequence of this SacI-XbaI fragment was determined and is presented in FIG. 3A. In FIG. 3B sequence homologies are shown to regions of the IgH, LPV, K-intron and SV40 enhancers as well as to the IFN response element (Samanta et al., 1986; Reid et al., 1989) and the conserved upstream sequence (CUS) of HLA-DQbeta that is implicated in gamma-IFN induction (Boss and Strominger, 1986). The E-boxes marked in the IgH comparison refer to the nomenclature used by Ephrussi et al. (1985). In the comparison of the K3'-enhancer with the $E_3^4$ region of the IgH enhancer, the dashed box shows the extended homology to uE3 and the arrows denote the inverted repeat of the uE$_3^4$ spacer as well as the region that flanks the 3' side of uE3.

Comparison with the sequences of other known enhancers revealed several striking homologies. The most extensive homology detected was with the enhancer region of the human lymphotropic papovavirus. There are two distinct regions of homology, a 17 out of 18 match and an 11 out of 12 match; both these elements are repeated within the origin region of the viral genome (Pawlita et al., 1985).

The other impressive homology is with a region around the E3 element of the IgH enhancer. Motifs (elements E1, E2, E3 and E4) within the IgH enhancer have been identified on the basis of the in vivo footprinting data (Ephrussi et al., 1985). The K3'-enhancer contains a segment showing a 12 out of 14 homology to the region of the IgH enhancer that has been shown to bind NF-uE3 (Sen and Baltimore, 1986; Peterson and Calame, 1987). Furthermore, the regions that flank either side of the E3 element in the IgH enhancer are also found to be present adjacent to the E3-like element of the K3'-enhancer but in a reshuffled form (FIG. 3B). Significant homologies are also found between the K-intron and K3'-enhancers. There are three separate 10 out of 11 matches: one overlaps the K-intron E3 element, another overlaps the K-intron E1 and the third homology includes within it a 7 out of 8 match to the octanucleotide element (Parslow et al., 1984; Falkner and Zachau, 1984) that has been identified in V gene promoters. In addition, sequence comparisons reveal an 8 out of 10 match to the NF-KB binding site, a sequence homologous to the consensus for the interferon response element (Samanta et al., 1986; Porter et al., 1988; Reid et al., 1989) and a homology to the conserved upstream sequence of the MHC class II genes, a sequence that may play a role in induction by gamma-IFN (Boss and Strominger, 1986). Several segments that show similarity to regions of the SV40 enhancer are also found (FIG. 3B).

The K3'-Enhancer is B Cell Specific

The homologies between the K3'-enhancer and other known enhancers led us to believe that it would be specifically active in lymphoid cells. To test this, assays we made of the activity of the enhancer in two non-lymphoid cell lines (NIH 3T3 and HeLa) as well as in three different lymphoid cell lines (the plasmacytoma MPC11; the B-cell line WEHI231 and the thymoma EL4). Cell-lines were transfected with the alpha-globin reference plasmid along with a pbeta128 derivative that included at position −128 either no enhancer (−), the SV40 enhancer (SV) or the 802 bp SacI-XbaI fragment containing the K3'-enhancer (K3'). mRNA levels were quantitated by ribonuclease protection assays as before. The results are given in FIG. 4, which shows that while the SV40 enhancer was active in all these lines, the K3'-enhancer was only active in the plasmacytoma and B cell lymphoma but not in the fibroblast or T cell lines. In other experiments (not shown), we have found that the enhancer is also inactive in another T cell lymphoma BW5147. Thus, the K3'-enhancer is B cell specific.

The K3'-Enhancer is Stronger than the K-intron Enhancer

The K-intron enhancer is known to be a weak enhancer. The activities of the K3', K-intron, IgH and SV40 enhancers were compared in transient transfection assays in the MPC11 myeloma. MPC11 cells were transfected with the alpha-globin reference plasmid plus either pbeta128 containing no enhancer (−), the SV40 enhancer (SV), the K3' or K-intron enhancer (K3', KIn) at position −128 or with a pbeta800 derivative containing the IgH enhancer at −800 (IgH). Globin transcripts. were mapped by ribonuclease protection assays, and the results are given in FIG. 5A. The results were quantitated by densitometry with each signal being normalized with respect to the alpha-globin mRNA levels. It was found that K3'-enhancer is sevenfold stronger than the K-intron enhancer but some twofold weaker than the SV40 enhancer. Direct comparison between these three enhancers and the IgH enhancer is not possible from these experiments as the IgH enhancer was placed at −800 with respect to the beta-globin start site whereas the other three enhancers were all assayed at −128. Nevertheless the results are consistent with those of Picard and Schaffner (1984) that the K-intron enhancer is some 20-fold weaker than the IgH enhancer and furthermore we clearly establish that the K3' enhancer is nearly an order of magnitude stronger than the K-intron enhancer when assayed in MPC11 cells.

The K3'-Enhancer is Deleted Upon RS Rearrangement

The location of the K3'-enhancer places it between the $C_K$ exon and the RS (rearranging sequence) element. FIG. 6B is a map of the mouse K locus showing the RS element as well as the rearranged RS allele of plasmacytoma MOPC315. The map of this rearranged RS is taken from Durdik et al. (1984). Restriction sites are abbreviated as in other Figures except that S indicates a Sau3AI site, although the only such sites depicted are those that were used to generate the rs0.8 fragment. Cells that express lambda light chains are usually found to have aberrant rearrangements involving the RS element on at least one of their K alleles and this can lead to deletion of $C_K$ (Durdik et al., 1984;

Moore et al., 1985). It would be expected that the K3'-enhancer would be deleted in these lines if RS rearrangement occurred by a simple looping-out mechanism. To confirm this, a Southern blot analysis was carried out of various lambda-expressing cell lines. DNA from BALB/c mouse liver, NIH 3T6 fibroblast cells and five mouse lambda-expressing lymphoid cell lines (129, BCL1, HOPC1, MOPC315 and CH-1) probed first for the K3'-enhancer (upper panel) and then reprobed for RS (lower panel). In this reprobing, G indicates the germline RS band of BALB/c whereas X is a cross-hybridising band. The genomic DNA was digested with EcoR1+BamH1 and the probe for the K3'-enhancer was an 3 kb EcoRI-BamHI fragment whereas the probe for RS was the rs0.8 probe of Moore et al. (1985). The blot is shown in FIG. 6A and revealed that several of the cell lines (HOPC1, BCL-1 and CH-1) retained at least one RS allele in germline configuration and, therefore, as is to be expected, retained at least one copy of the K3'-enhancer. The case of 129 is difficult to interpret as the mouse strain from which this lymphoma derives shows considerable restriction map differences from the BALB/c strain (Stavnezer et al., 1985) and the difference in the sizes of restriction fragments could therefore reflect polymorphism rather than rearrangement. However, the MOPC315 myeloma does not retain an RS allele in germline configuration and has entirely deleted the K3'-enhancer from its genome (FIG. 6A, B). The interrupted line in FIG. 6B indicates the postulated simple looping out that could have given rise to the MOPC315 RS rearrangement. This strongly suggests that the RS rearrangement is itself responsible for the loss of the enhancer and that RS recombination does indeed lead to enhancer deletion.

High Level Expression in Transgenic Mice of K Genes That Include the 3'-Enhancer Transgenic mouse lines were established in order to ascertain whether sequences located downstream of $C_K$ affected K gene expression. The transgenes were composed of a mouse $V_K$ gene linked to a rat $C_K$. The presence of the rat constant region meant that the transgene could be distinguished from the endogenous K at the protein level using anti-rat K antibodies and at the nucleic acid level by a ribonuclease protection assay. The V-region was characteristic of antibodies directed against the hapten phenyl-oxazolone. Two transgenes were used: a long one (LK) which includes both the intron- and 3'-enhancers and a short one (SK) which contains only the intron-enhancer. The two gene constructs are shown in FIG. 7. In the Figure sequences of mouse origin are shown thickly stippled, rat sequences are shown thinly stippled and enhancers are in open boxes. Four lines of transgenic mice which harboured between 2 and 5 copies of the transgene (SK[2], SK[4], LK[3] and LK[6]) were used for most of the analyses, although a high-copy (SK[5]) line which carried 30–50 copies of the short K construct was also included for comparison.

Transgene expression of the K gene was analysed by immunofluorescence of splenic B cells from adult transgenic mice. The results are given in FIG. 8 which shows histograms depicting the percentaged K+ cells in the spleens of the adult transgenic mice that stained for either: transgenic rat K and endogenous mouse (TGK+,EK+); transgene K only (TGK+,EK−) or endogenous K only (TGK−,EK+). In SK[4] animals carrying the short K construct, transgene expression was weak as judged by the intensity of the fluorescence and was only detectable in some 5–7% of splenic B cells; nearly all the B cells expressed an endogenous mouse light chain (FIG. 8). A similar pattern of expression was found in the SK[2] mice (not shown). The low level of expression can to some extent be compensated for by a large increase in transgene copy number as in SK[5] mice a greater proportion of the B cells stained for the transgene (FIG. 8).

The results obtained with the long K construct contrast sharply with those obtained with the short one. In the LK[3] line, 80–85% of the adult splenic B-cell population expressed only the transgene, with the remaining 10–15% of the B cells coexpressing an endogenous light chain (FIG. 8). Transgene expression is even more dominant in the LK[6] line with about 90% of the splenic B cells expressing only rat CK. Thus expression levels from the long K construct are sufficient to effect allelic exclusion.

The difference between the transgenes is also evident from the titres of serum antibody. ELISA assays reveal that whereas the titre of antibody containing transgenic K chains in adult SK[2] and SK[4] mice is about 100 ug/ml, the corresponding titre in the LK mice is some 10–50 fold higher. However, the major contribution of cellular selection in determining the overall in vivo pattern of transgene expression (Pettersson et al., 1989) makes such comparisons of serum titres very crude. We therefore compared transgene expression in hybridomas generated by fusing spleen cells from the transgenic mice with the NSO plasmacytoma. Supernatants of hybridoma cells grown to saturation in DMEM/10% FCS were assayed for rat K determinants. Titres are given as the dilution of supernatant required to react with the sequester 50% of the anti-rat K antibody used in the ELISA. The assays have been carried out several times; in each batch of assays of hybridoma supernatants from the same mouse line, the scatter of individual titres was such that the s.e.m. always amounted to less than 25% of the mean. The results are given in FIG. 9. As regards both the LK[3] and LK[6] mice, the pattern of light chain expression in the hybrids paralleled what was observed in the immunofluorescence analysis of the splenic B cells. In other words, over 80% of the hybrids synthesised the transgenic light chain and made no mouse K. In contrast, in the SK[4] mice we found that an endogenous mouse light chain was co-expressed by over 80% of the transgene hybrids; the same held true for the SK[2] mice. Presumably the difference in the results obtained from the analysis of transgene expression in the primary B cells of the SK mice from those obtained from analysis of light chain expression in hybridomas reflects the fact that the expression of the transgene in primary cells is below our level of detection; this low level, however, is increased on fusion. From the results shown in FIG. 9 it will be seen that transgene expression in the hybridomas from the LK mice is some 20–50 fold higher than from the SK mice. Thus, the short K transgene is only poorly expressed and is relatively ineffective in mediating feedback inhibition of endogenous light chain gene rearrangement. However, results with the long K construct show that sequences downstream of the constant region have a dramatic effect on increasing K gene expression in transgenic mice and allowing effective allelic exclusion of endogenous K expression.

The 3'-Enhancer Increases K Expression in Stably Transfected Plasmacytoma

It is presumed that the 3'-enhancer is responsible for the increased transcriptional activity of the long as opposed to the short K construct. In order to test this directly, we resorted to stable transfection assays in the NSO plasmacytoma as illustrated in FIG. 10.

Figure 10B:
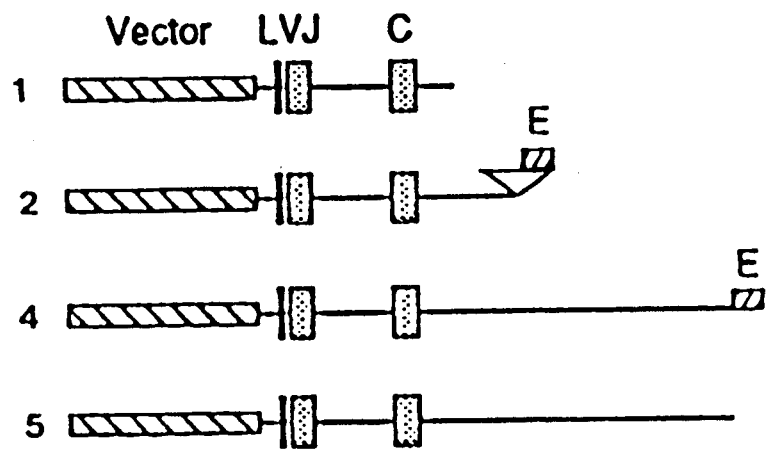
Figure 10C:
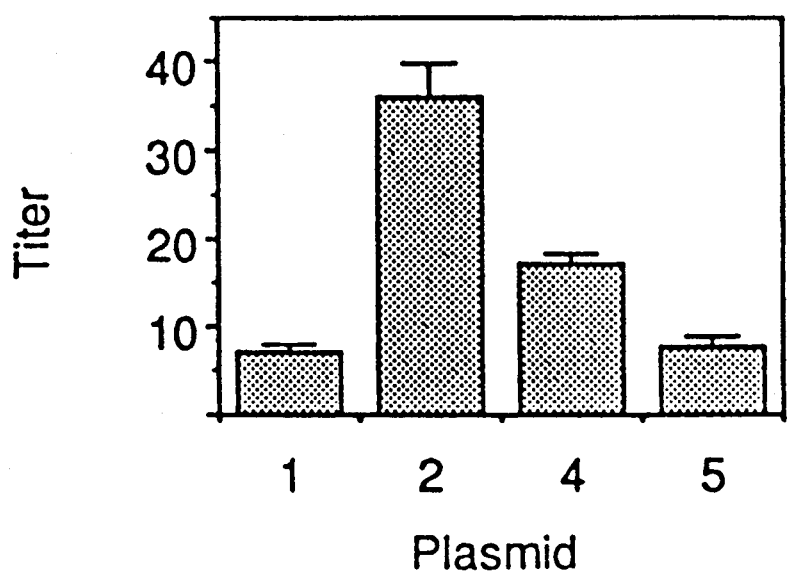

A series of constructs with and without the 3'-enhancer were generated. The plasmids used are illustrated in FIG. 10B. All the constructs are based on the "long" K construct depicted in FIG. 7. Plasmid 1 contains the EcoRI-BamHI $V_K$-$C_K$ segment of the long construct cloned between the EcoRI and BamHI sites of pSV2neo; the BamHI site is located 1.2kb downstream of the $C_K$ polyadenylation site; plasmid 2 was created by digesting plasmid 4 with EcoRV and self-ligation; plasmid 4 is the long construct depicted in FIG. 7 cloned into the EcoRI site of pSV2neo; plasmid 5 carries the EcoRI-XhoI $V_K$-$C_K$ segment of the long construct cloned between the EcoRI and XhoI sites of a pSV2neo-derivative that has XhoI linkers in the BamHI site.

The constructs, 1, 2, 4 and 5 of FIG. 10B were transfected into NSO cells and rat K expression in pools of stable transfectants was measured by ribonuclease protection assays. For each construct, transcripts of the transfected and endogenous K genes were assayed in samples of RNA that were prepared from pools of 12 wells each of which contained multiple clones. The results are shown in FIG. 10A. The positions of size markers (a HpaII digest of pBR322) are shown in the lane marked "M". Sterile transcripts from the endogenous, aberrantly rearranged K gene of NSO cross-hybridised with the probe and served as an internal control.

It is clear that expression from constructs 2 and 4 (which include the 3'-enhancer) was significantly higher than from constructs 1 and 5 (which do not). Thus, the 3'-enhancer enhancer makes a difference to K gene expression in stably transfected plasmacytoma. The effect is considerably less than that observed with the transgenic mice. This is scarcely surprising as the K transcription unit in the transfected NSO is linked to the active neogene with its adjacent SV40 enhancer; this could compensate to some degree for the lack of the downstream enhancer in constructs 1 and 4.

To ensure that the expression levels seen in ribonuclease protection assays from the mixed populations are not biased due to differential outgrowth of specific clones, we analysed serum titres of rat K chains in individual wells which represent distinct integration events. Expression of the transgenic K chain in supernatants of individual wells of NSO transfectants is depicted as a histogram in FIG. 10C. Cells were grown to saturation in DMEM/10% FCS. Titres are given as the dilution of the culture supernatant that is required to react with and sequester 50% of the anti-rat K antibody used in the ELISA; the s.e.m. is indicated by error bars. The results reflect those seen with the pools.

Functional Dissection of the 3'-Enhancer

Thus the 3'-enhancer does indeed appear to play a role K gene expression. The induction of K transcription in several pre-B cell lines is known to correlate with the activation of the intron enhancer and the translocation of one of its cognate binding factors (NF-KB) into the nucleus (REFS). We have previously noted the presence of a sequence related to the NF-KB binding motif in the region of the 3'-enhancer (Meyer and Neuberger, 1989); further work was therefore carried out to delimit the active part of the 3'-enhancer more precisely and in order to discover whether the activation of the intron- and 3'-enhancers could be induced by a common mechanism.

The 808 base pair SacI-XbaI 3'-enhancer fragment of FIG. 3 was subcloned and linked to a human beta-globin gene, which served as reporter gene in transient transfection assays. FIG. 11A is a map showing the subfragments a–f of the 808bp SacI-XbaI K3'-enhancer that were assayed for activity. Restriction sites are abbreviated: S,SacI;Sp,SspI;N,NcoI;Bx,BstXI;H,HaeIII and St,StyI. For the latter two enzymes, only relevant sites are shown. The solid boxes represent sequence homologies identified to the IgH-intron and the K-intron enhancers. The plasmid pbeta128 used for the enhancer assays is shown schematically in FIG. 11B. The constructs carrying the inserts a–f shown in FIG. 11 were transfected into the MPC11 plasmacytoma along with a human alpha-globin reference plasmid; cytoplasmic RNA was prepared 38–42 hrs after transfection. The amount of beta- and alpha-globin RNAs were measured by ribonuclease protection assays and the results are shown in FIG. 11C for the pbeta128 derivatives carrying enhancer subfragments a–f, the SV enhancer (SV) or no enhancer (—) at position —128 of pbeta128.

Comparison of the activities of the various subfragments reveals that full activity was contained with a 145 base pair region (fragment f). Not only does fragment f not include the sequence homologous to the NF-KB binding site, but the homologies that we had previously noted to the E2/E3 region of the mouse IgH intron-enhancer as well as to the interferon consensus are also absent from this region. Thus the activity of the enhancer must be caused by sequence motifs that we had not previously identified on the basis of homology searches. To locate such motifs more precisely, we made a number of approximately 20 base pair deletions within fragment f by site-directed mutagenesis. Internal deletions were made within enhancer subfragment f with the following deletion endpoints using the numbering of Meyer and Neuberger (1989): delta1 deletion (nt 389–411, data not shown); delta2 (nt 416–436); delta3 (nt 437–456); delta4 (nt 457–471) and delta5 (nt 476–489). The deleted DNA was substituted by the sequence CTCGAG. The deletions are illustrated in FIG. 12B. The nucleotide sequence shown in FIG. 12B is listed as SEQ ID NO:3. SEQ ID NO:3, absent the 3' terminal TTTC sequence, forms SEQ ID NO:1.

MPC11 cells were transfected with a Bluescript KS+ vector (Stratagene) carrying enhancer subfragment f or its deletion derivatives placed 128 nt upstream of the human beta-globin gene along with an alpha-globin reference plasmid. Globin transcripts were mapped by ribonuclease protection assays and the results given in FIG. 12A. Enhancer activity is not impaired by deletions 1 or 2, but deletions 3, 4 and 5 abolish function. Interestingly delta3 spans a sequence (TTTGAGGAA) which shows good homology to a region of the mouse IgH enhancer (TTTGGGGAA) that binds a nuclear factor and is implicated in lymphoid-specific transcriptional activity (Araki et al., 1988).

The 3'-Enhancer Allows K Expression in S107 Cells Which Lack NF-KB

Since the activity of the 3'-enhancer could be located to a region that does not include homology to the NF-KB binding motif, NF-KB is presumably not required for its function. Therefore, the 3'-enhancer might well account for the transcriptional activity of the endogenous K gene of S107, a plasmacytoma cell line which lacks functional NF-KB, does not activate the K-intron enhancer and in which many transfected K genes are silent (Atchinson and Perry, 1987). To test this, we stably transfected S107 cells with 3 constructs illustrated in FIG. 13B that carried the rearranged K gene with or without the 3'-enhancer. Expression of the transfected K gene was analysed by ribonuclease protection assays from pools of stable transfectants RNA was prepared from pools of 24 wells. Plasmids 1 and 2 are described above in connection with FIG. 10; plasmid 3 was derived from the plasmid 4 by internal deletion using ClaI and XhoI. The assay results are given in FIG. 13A.

Whereas constructs 2 and 3 which both carry the 3'-enhancer were transcribed at high levels, the expression of construct 1 is scarcely detectable. To ensure that the high levels of transcription seen for construct 2 and 3 were not due to single positive clones having outgrown an otherwise negative population, we assayed individual wells and found that for both these constructs all wells tested were positive for rat $C_K$ with high, but somewhat variable expression levels. In sharp contrast, expression levels of construct 1 were below the levels of detection in all wells tested. These results strongly support the proposal that it is the 3'-enhancer which drives expression of the endogenous K gene of S107 and demonstrates that NF-KB is indeed not required for the activity of this enhancer. Interestingly, the presence of the SV40 enhancer in the vector is not able to compensate for the lack of the 3'-enhancer in construct 1; this is in keeping with the fact that the SV40 enhancer is relatively weak in S107 cells, possibly because its activity in plasmacytoma cells depends considerably upon NF-KB (Atchinson and Perry, 1987).

Materials and Methods

DNA and Plasmids

The phase lambda clone L1 (Steinmetz et al., 1979) containing the germline mouse K locus was a gift from H. Zachau and plasmids pbeta128, pbeta800 and piSVHPalpha2 (Treisman, 1985) were from R. Treisman and K. Weston. A pbeta800 derivative with a 1 kb XbaI fragment containing IgH enhancer at −800 and a pbeta128 derivative with the SV40 enhancer at −128 were gifts from K. Weston. A pbeta128 derivative containing a 481 bp Sau3AI fragment spanning the K-intron enhancer at position −128 was a gift from Graham Cook. The plasmid containing the RS probe (rs0.8 of Moore et al., 1985) was provided by E. Selsing. The short K construct used for creating the SK transgenic mice has been previously described (Pettersson et al., 1989). For the creation of the long construct, a rat $C_K$ fragment of the LOU allele (Sheppard and Gutman, 1981) was modified by site directed mutagenesis (Carter et al., 1985) to create HpaI and BglII sites at positions corresponding to those found in mouse $C_K$ (Max. et al., 1981). The 470 nt HpaI-BglII rat $C_K$ fragment was then excised and this fragment ligated in place of the equivalent mouse $C_K$ fragment in a mouse genomic XbaI-BamHI subclone in pUC18. This composite $C_K$ was combined with the rearranged mouse $V_KOx$-1 (1.4kb EcoRI-XbaIZ to form a 5.2 kb EcoRI-BamHI fragment in a pUC vector with a SmaI site flanking the BamHI. An 8kb SacI-EcoRI fragment containing mouse genomic DNA downstream of $C_K$ (including the K3'-enhancer) was subcloned into pUV18, excised as a SmaI-EcoRI fragment, and ligated together with the 5.2kb $V_KOx$-1/composite-$C_K$EcoRI-SmaI fragment in the EcoRI site of the vector pSV2neo.

Derivatives of the long construct that differed in the $C_K$ 3'-region were created as described above. For deletion analysis of the 3'-enhancer, deletions within fragment f were generated using a Bluescript KS+ vector; single-stranded DNA was prepared by superinfection with helper virus and site directed mutagenesis carried out as described elsewhere (Carter et al., 1985).

Cell Lines, Cell Culture and DNA Transfection

Myelomas HOPC1 (Weigert et al., 1970) and MOPC315 (Eisen et al., 1968) and the CH-1 B cell lymphoma (Lanier et al., 1978) were obtained from the American Type Culture Collection, MD, USA. The BCL1 line was given to us by Ellen Vitetta, 129 by Roberto Sitia, HeLa by Richard Treisman and MPC11 BU4 by B. Wasylyk. The WEHI231, BW5147, NIH 3T3 and EL4 cells were from our lab collection and their origin is as previously described (Mason et al., 1985). All cells were grown in DMEM/10% FCS/50 uM 2-mercaptoethanol except that RPMI medium was used for CH-1, 129 and BCL1. The MPC11, BW5147, HeLa and NIH-3T3 cells were transfected by calcium phosphate coprecipitation (Graham and van der Eb, 1973) using 20 ug of test plasmid and 5 ug of piSVHP2 internal reference. Transfection of WEHI231 and EL4 was achieved by use of DEAE-dextran as previously described (Mason et al., 1985). Cells were harvested 36–42 h after transfection.

Preparation and Analysis of RNA and DNA

Total cytoplasmic RNA was prepared and ribonuclease protection assays (Melton et al., 1984) carried out as previously described (Mason et al., 1985). DNA from mamalian cells for analysis by Southern blotting was prepared by phenol extraction of whole cell lysates made using lithium dodecyl sulphate. For sequencing of the K3'-enhancer, subclones were generated in M13mp18 or M13mp19 and sequenced by the chain termination method of Sanger et al. (1977) except that the extension was catalysed by Sequenase (United States Biochemical Corporation). The region was sequenced on both strands.

Transgenic Mice and Hybridomas

Derivation of transgenic mice lines carrying the SK construct has been described (Pettersson et al., 1989, Sharpe et al., 1990). Previously these have been referred as KOx lines, but in this work $KOx^2$ is designated $SK^2$, $KOx^4$ is $SK^4$ etc. The LK mice were generated by microinjection of a vector-free EcoRI 13.5 kb fragment into the pronucleus of (C57BL/6×CBA) female×(C57BL/6×CBA) male eggs as previously described (Reik et al., 1987). Positive offspring were identified by Southern blot analysis of tail DNA or by serum ELISA and bred with BALB/c mice. Hybridomas were established from adult mice by fusion of spleen cells with the myeloma NSO (Galfre and Milstein, 1981).

Serological Assays and Immunofluorescence

Transgenic K chains were detected by an ELISA using the mouse anti-rat K monoclonal antibody MARK-1 as previously described (Pettersson et al., 1989). Cytoplasmic immunofluorescence of permeabilised spleen cells attached to slides (Pettersson et al., 1989) was performed using FITC-conjugated OX-20 (Serotec) to detect mouse K; to detect transgenic K, we used biotinylated sheep anti-rat antiserum in the presence of 1% normal mouse serum chain followed by streptavidin conjugated to TEXAS-red (Amersham).

DNA Transfection and Ribonuclease Protection Assay

MPC11 BU4 was obtained from B. Wasylyk; S107 (originally from the Salk Cell Bank) and NSO (Clark and Milstein, 1981) from our laboratory culture collection and maintained in Dulbecco's modified Eagle's medium containing 10% foetal calf serum. Stable transfection was achieved by electroporation (Potter et al., 1984); the S107 and NSO transformants were selected 24 h after transfection by resistance to G418 (Gibco) at an initial concentration of 0.5 mg/ml and this selective concentration increased to 1 mg/ml (S107) or 2 mg/ml (NSO) 6 days after transfection. MPC11 was transiently transfected by calcium phosphate coprecipitation (Graham and van der Eb, 1973) and total cytoplamic RNA was prepared by NP40 lysis and subsequent phenol extraction of the cytosolic fraction 38–42 h later. Ribonuclease protection assays (Melton et al. 1984) were carried out as described previously (Mason et al., 1985).

Somatic Hypermutation Occurs in the Long (LK) but not the Short (SK) Version of an Immunoglobin K Light Transgene Further experiments were carried out with transgenic mice carrying the short and long constructs described above in connection with FIG. 7. The SK series contains the 'short' construct that extends 1kb downstream of the $C_K$ gene, and the LK series contains a 'long' construct that extends 9kb downstream of the $C_K$ gene and includes the mouse K3'-enhancer. The transgene V-region is directed against the hapten 2-penyl oxazolone (phOX) and in combination with the appropriate endogenous mouse heavy (H) chain produces an anti-phOX antibody. For each construct, transgenic mice which contain a low number of copies of integrated DNA have been analysed to see whether the transgene V-region can undergo somatic hypermutation during the immune response to phOX.

In order to invoke a typical secondary immune response accompanied by somatic hypermutation of antibody genes, adult mice heterozygous for the transgene were immunised intraperitoneally with alum-precipitated phOX coupled to chicken serum albumin (phOX$_{17}$CSA,30–100 ug) together with $10^9$ heat-killed Bordetella pertussis bacteria and were then boosted after 7 weeks with an intravenous injection of soluble phOX$_{17}$CSA (30–100 ug). Splenic hybridomas were established by fusion with the NSO plasmacytoma 3 days after boosting. Following the use of an ELISA assay on culture supernatants, antigen-specific B-cell hybridomas were isolated and the sequence of the transgene V-region determined by specific cDNA cloning from transgene mRNA. The cDNA cloning was performed by incubating poly(A)+RNA from the relevant hybridomas with AMV reverse transcriptase, dNTPs and an antisense oligonucleotide which hybridised to the 3'-region of either the rat (transgene) or mouse (endogenous) $C_K$. Full length cDNA was eluted from a denaturing polyacrylamide gel. The polymerase chain reaction was then used to amplify the first strand material using oligonucleotides that hybridised to the 5'-end of $V_KOX$ and the 3'-end of mouse or rat $C_K$. Amplified cDNA was cloned into vectors M13mp18 or M13mp19 for subsequent sequencing by the dideoxy method. The sequences of cDNAs derived from both the transgenic K genes and the endogenous mouse antibody genes within the same hybridomas were determined in order to confirm that the hybrids were derived from B-cells in which hypermutation had occurred. Sequences of the expressed $V_H$ segments of the hybridomas were determined by a procedure analogous to that used for $V_K$.

For the SK mice, two independent lines (SK$^2$ and SK$^4$) have been analysed in detail. Low levels of expression of this construct in transgenic mice and the corresponding lack of allelic exclusion result in hybridomas which co-express an endogenous mouse light chain in addition to the transgene light chain (see above). In order to assess whether somatic mutation had been active in the phOX-specific B-cells, the sequences of the endogenous mouse H and K chains in several transgenic hybridomas were analysed by cloning of PCR amplified first strand cDNA. FIG. 14 shows sequence mutations endogenous light (FIG. 14A) and endogenous heavy (FIG. 14B) chain V region genes in anti-phOX hybridomas from transgenic mice SK$^2$ (NQT3-) or SK$^4$ (NQT8-). The top line shows the sequence of the germline $V_K$-OX1 or the germline $V_H$-OX1. The amino acid translation is given above. Numbers in bold type indicate amino acids in the complementarity determining regions. Sequences of six individual hybridoma clones are given below, and only the positions exhibiting nucleotide differences with germline genes $V_H$-OX1 and $V_K$-OX1 are shown. —, identity with germline sequence; , probable identity; 3, probably A; a gap indicates that the nucleotide could not be identified or was not sequenced in this region. Predicted coding changes are indicated. Four hybrids were derived from the SK$^2$ line (NQT3 fusion) and three from the SK$^4$ line (NQT8 fusion). Six out of the seven hybridomas express the idiotypic $V_H$-OX1/$V_K$-OX1 gene combination, while one (NQT8/L1.10) uses a different $V_H$ gene together with a $V_K$ of hybridoma NQ10/4.6.1. The six hybridomas with the $V_H$-OX1/$V_K$-OX1 idiotype all contain nucleotide changes from germline BALB/c sequences and both coding and non-coding changes are found.

The light chain V region sequences include changes which are typical of somatic mutations seen in the phOX response in BALB/c. For example, the region around amino acids 34 and 36 of the light chain has been identified as a potential mutational 'hotspot' (see Berek and Milstein; 1987). The heavy chain V-regions, including the non-$V_H$-Ox1 sequence from NQT8/L1.10, display the features typical of anti-phOX genes, namely a DJ region 16 amino acids in length of which the first residue of the D is Asp and the third a Gly. Nucleotide changes in the $V_H$-OX1 V regions include a characteristic Set to Thr changes at position 31 in CDR1 (see Berek and Milstein; 1987) in NQT3/C13.1, NQT3/H15.6 NQT8/E10.1 and NQT8/L20.4. In summary, all seven hybridomas display evidence of somatic mutations in the endogenous heavy and light chain genes. The frequency of nucleotide changes averages 3 per light chain and 4 per heavy chain.

The transgene sequence in the same phOX-specific hybridomas was determined from cDNA clones generated by PCR amplification of specifically primed first-strand cDNA. As the mice contain two (KOX[2]) or four (KOX[4]) copies of transgene, and it is not known how many of these are transcribed, 10 to 20 cDNA clone V regions (350 bp each) were sequences from each hybridoma. The corresponding C regions (270bp each) of about half of these clones were also sequences. cDNA sequences were compared to that of the introduced gene. FIG. 15 shows nucleotide changes in transgene cDNA clones from anti-phOX hybridomas from transgenic mice SK[2] (NQT3-) or SK[4] (NQT8-). The top line shows the sequence of the transgene $V_K$-Ox1 V region and the rat C kappa region with amino acid translation given above. Numbers in bold type indicate amino acids in the complementarity determining regions. Sequences of cDNA clones derived from seven hybridomas are given below. Only the codon position which showed nucleotide differences from the transgene are shown. Dashes indicate identity with the original sequence, a gap indicates that the sequence was not determined in this region. cDNA clones which exhibit a nucleotide change are individually numbered; those in which there were no changes at all are grouped together according to whether the V region only, or both the V and the C region, were sequenced. If a copy of the transgene has mutated, one would expect the same sequence change to be encountered several times in 10-20 cDNA clones. On the other hand, of no somatic mutations have occurred, then the sequences should be identical except for random base changes introduced as cloning errors during the first-strand synthesis and PCR. As none of the nucleotide substitutions in FIG. 15 was observed as a repeat, we conclude that they all arose as cloning artefacts. The frequency of nucleotide changes seen in the V domains is similar to that seen in the C domains ($3-6 \times 10^4$ per bp, FIG. 15), and this frequency is in the order of the error rates expected for reverse transcriptase and Taq polymerase.

Thus endogenous mouse H and L chain V-regions from seven anti-phOX hybridomas were found to be mutated. However, the transgene V-region from the same hybridomas showed no somatic mutation at all. Thus it would appear that the transgene $V_K$-OX1 sequence has not been altered by somatic mutation in these hybridomas from either of the two KOX transgenic mouse lines although the somatic mutation process had occurred in these cells.

For the LK mice, several hybridomas have been analysed from the LK[3] line in the same way as the SK hybridomas were analysed. High levels of expression of this construct in transgenic mice result in increased allelic exclusion and the majority of anti-phOX hybridomas express solely the transgenic light chain with an endogenous mouse heavy chain (see above). In striking contrast to the SK mice, the first 3 anti-phOX hybridomas analysed from line LK[3] all contain sequence changes in the transgene V-region. FIG. 16 shows nucleotide changes in transgene cDNA clones from anti-phOX hybridomas (mouse link LK[3]). cDNA clones were generated by PCR amplification of specifically primed first-strand cDNA. V-region sequences of 10 cDNA clones from each hybridoma are grouped according to the pattern of nucleotide changes. Positions at which a base change was encountered in only one of the 10 sequences have been ignored as these are likely to reflect cloning errors rather than true mutations. Numbering of the transgene $V_K$-OX1 V-region codons is the same as above. Dashes indicate identity with the original sequence, a gap indicates that the sequence was not determined in this region. No mutations are seen in the corresponding C-regions, consistent with the normal in vivo targeting of somatic mutations to V-regions only. Line LK[3] carries about 4 copies of the construct; from the distribution of nucleotide changes, it seems that each copy is mutated independently of the others and at least 2 or 3 of the copies are transcribed.

In conclusion, the presence of the 8kb region of genomic DNA which includes the K3'-enhancer appears to be necessary in vivo both for high expression and for somatic hypermutation of Ig light chain transgenes.

References

Araki, K., Maeda, H., Wang, J., Kitamura, D. and Watanabe, T.(1988) Cell 53, 723–730.

Atchinson, M. L. and Perry, R. P. (1987) Cell 48, 121–128.

Atchinson, M. L. and Perry, R. P. (1988) EMBO J. 7, 4213–4220.

Banerji, J., Olson, L. and Schaffner, W. (1983) Cell 33, 729–740.

Berek, C. and Milstein, C. (1987) Immunological Reviews 96,23.

Boss, J. M. and Strominger, J. L. (1986) Proc. Natl. Acad. Sci. USA 83, 9139–9143.

Carter, P. Bedouelle, H. Waye, M. M. Y. and Winter, G. (1985) Oligonucleotide site-directed mutagenesis in M13, An experimental manual Anglian Biotechnology Limited.

Clarke, M. R., and Milstein, C. (1981) Somatic Cell Genet. 7, 657

Durdik, J., Moore, M. W. and Selsing, E. (1984) Nature 307, 749–752.

Eisen, H. N., Simms, E. S. and Potter, M. (968) Biochemistry 7, 4126–4134.

Ephrussi, A., Church, G. M. Tonegawa, S. and Gilbert, W. (1985) Science 227, 134–140.

Falkner, F. G. and Zachau, H. G. (1984) Nature 310, 71–74.

Galfre, G. and Milstein, C. (1981) Meth. in Enzymol. 73, 3–46.

Gillies, S. D., Morrison, S. L., Oi, V. T. and Tonegawa, S. (1983) Cell 33, 717–729.

Graham, R. and van der Eb, A. (1973) Virology 52, 456–467.

Klobeck, H.-G., Zimmer, F.-J., Combriato, G. and Zachau, H. G. (1987) Nucl. Acids Res. 15, 9655–9665.

Lanier, L. L., Lynes, M. and Haughton, G. (1979) Nature 271, 554–555.

Mason, J. O. Williams, G. T. and Neuberger, M. S. (1985) Cell 41, 479–487

Max, E. E., Maize, J. V. Jr. and Leder, P (1981) J. Biol.Chem 56, 5116

Melton, D. A., Krieg, P. A. Rebagliati, M. R., Maniatis, T., Zinn, K. and Green, M. R. (1984) Nucl. Acids Res. 12, 7035–7056.

Meyer, K. B. and Neuberger, M. S. (1989) EMBO J. 8, 1959–1964.

Moore, M. W., Durdik, J., Persiani, D. M. and Selsing, E. (1985) Proc. Natl. Acad. Sci. USA 82, 6211–6215.

Neuberger, N. S. (1983) EMBO J. 2, 1373–1378.

Parslow, T. G., Blair, D. L., Murphy, W. J. and Granner, D. K. (1984) Proc. Natl. Acad. Sci. USA 81, 2650–2654.
Peterson, C. and Calame, K. L. (1987) Mol.Cell Biol. 7, 4194–4203.
Pettersson, S., Sharpe, M. J., Gilmore, D. R., Surani, M. A. and Neuberger, M. S. (1989) Int. Immunol. 1, 509–516.
Pawlita, M., Clad, A. and zur Hausen, H. (1985) Virology 143, 196–214.
Porter, A. C. G., Chernajovsky, Y., Dale, T. C., Gilbert, C. S., Stark, G. R. and Kerr, I. M. (1988) EMBO J. 7, 85–92.
Picard, D. and Schaffner, W. (1984) Nature 307. 80–82.
Potter, H. Weir, L. and Leder, P. (1984) Proc.Natl.Acad.Sci. USA 81, 7161–7165.
Queen, C. and Baltimore, D. (1983) Cell 33, 741–748.
Queen, C. and Stafford, J. (1984) Mol. Cell Biol. 4, 1042–1049.
Reid, L. E., Brasnett, A. H., Gilbert, C. S., Porter, A. C. G., Gewert, D. R., Stark, G. R. and Kerr, I. M. (1989) Proc. Natl. Acad. Sci. USA 86, 840–844.
Reik, W., Williams, G. Barton, S. Norris, M., Neuberger, M. and Surani, M. A. (1987) Eur. J. Immunol. 17, 465–469.
Rusconi, S. and Kohler, G. (1985) Nature 314, 330–334.
Samanta H., Engel, D. A., Chao, H. M., Thakur, A., Garcia-Blanco, M. A. and Lengyel, P. (1986) J. Biol. Chem 261.11849–11858.
Sanger, F., Nicklen, S. and Coulson, A.R. (1977) Proc. Natl.Acad. Sci. USA 74, 5463–5467.
Sen, R. and Baltimore D. (1986) Cell 46, 705–715.
Sharpe, M. J., Neuberger, M. Pannell, R. Surani, M. A. Milstein, C. (1990) Eur. J. Immunol. in the press.
Sheppard, H. W. and Gutman, G. A. (1981) Proc. Natl. Acad. Sci. USA 78, 7064–7068.
Steinmetz, M., Zachau, H. G. and Mach, B. (1979) Nucl.Acids Res. 6, 3213–3229.
Stavnezer, J., Sirlin, S. and Abbott, J. (1985) J. Exp. Med. 161, 577–601.
Triesman, R. H. (1985) Cell 42, 889–902.
Wabl, M. and Burrows, P. D. (1984) Proc .Natl. Acad. Sci. USA 81, 2452–2455.
Weigert, M. G., Cesari, I. M., Yonkovitch, S. J. and Cohn, M. (1970) Nature 228, 1045–1047.

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
AGAAGACCCT TGAGGAACT GAAAACAGAA CCTTAGGCAC ATCTGTTGC            49
```

( 2 ) INFORMATION FOR SEQ ID NO:2:

( i ) SEQUENCE CHARACTERISTICS:
        ( A ) LENGTH: 808 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
AGCTCAAACC AGCTTAGGCT ACACAGAGAA ACTATCTAAA AAATAATTAC TAACTACTTA    60
ATAGGAGATT GGATGTTAAG ATCTGGTCAC TAAGAGGCAG AATTGAGATT CGAACCAGTA   120
TTTTCTACCT GGTATGTTTT AAATTGCAGT AAGGATCTAA GTGTAGATAT ATAATAATAA   180
GATTCTATTG ATCTCTGCAA CAACAGAGAG TGTTAGATTT GTTTGGAAAA AAATATTATC   240
AGCCAACATC TTCTACCATT TCAGTATAGC ACAGAGTACC CACCCATATC TCCCACCCA    300
TCCCCCATAC CAGACTGGTT ATTGATTTTC ATGGTGACTG GCCTGAGAAG ATTAAAAAAA   360
GTAATGCTAC CTTATTGGGA GTGTCCCATG GACCAAGATA GCAACTGTCA TAGCTACCGT   420
CACACTGCTT TGATCAAGAA GACCCTTTGA GGAACTGAAA ACAGAACCTT AGGCACATCT   480
GTTGCTTTCG CTCCCATCCT CCTCCAACAG CCTGGGTGGT GCACTCCACA CCCTTTCAAG   540
TTTCCAAAGC CTCATACACC TGCTCCCTAC CCCAGCACCT GGCCAAGGCT GTATCCAGCA   600
```

CTGGGATGAA AATGATACCC CACCTCCATC TTGTTTGATA TTACTCTATC TCAAGCCCCA          660

GGTTAGTCCC CAGTCCCAAT GCTTTTGCAC AGTCAAAACT CAACTTGGAA TAATCAGTAT          720

CCTTGAAGAG TTCTGATATG GTCACTGGGC CCATATACCA TGTAAGACAT GTGGAAAAGA          780

TGTTTCATGG GGCCCAGACA CGTTCTAG                                             808

( 2 ) INFORMATION FOR SEQ ID NO:3:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

AGAAGACCCT TGAGGAACT GAAAACAGAA CCTTAGGCAC ATCTGTTGCT TTC                   53

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

ACCTGCTCCC TACCCCACCA CCTGGCCAAG GCT                                       33

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CAGCTGGCAG GAAGCAGGTC ATGTGGC                                              27

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

AAGGCTATTT GGGGAAGG                                                        18

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GGTTAGTCCC CAGTCCC                                                              17

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GGAAAGTCCC CAGGCTC                                                              17

(2) INFORMATION FOR SEQ ID NO:9:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GGAAAGTCCC C                                                                    11

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CTTTCAAGTT TCCAAAGC                                                             18

(2) INFORMATION FOR SEQ ID NO:11:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

AAGTTTGCAA AGC                                                                  13

(2) INFORMATION FOR SEQ ID NO:12:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

ATCCAGCACT GG                                                                   12

(2) INFORMATION FOR SEQ ID NO:13:

(i) SEQUENCE CHARACTERISTICS:
        (A) LENGTH: 12 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:13:

AATCAGCACT GG  12

(2) INFORMATION FOR SEQ ID NO:14:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:14:

AGTATTTTCT ACCTGGTAT  19

(2) INFORMATION FOR SEQ ID NO:15:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:15:

AGTTTTTTCT ACCTGGTAT  19

(2) INFORMATION FOR SEQ ID NO:16:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:16:

TCTGCAACAA CA  12

(2) INFORMATION FOR SEQ ID NO:17:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:17:

TCTGCAAAAA CA  12

(2) INFORMATION FOR SEQ ID NO:18:

(i) SEQUENCE CHARACTERISTICS:
(A) LENGTH: 13 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:18:

TATTGATTTT CAT                                                                  13

( 2 ) INFORMATION FOR SEQ ID NO:19:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

TATTGTTTTT C                                                                    11

( 2 ) INFORMATION FOR SEQ ID NO:20:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

AGTGTCCCAT G                                                                    11

( 2 ) INFORMATION FOR SEQ ID NO:21:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

ATTGTCCCAT GTTGT                                                                15

( 2 ) INFORMATION FOR SEQ ID NO:22:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

AGCAACTGTC A                                                                    11

( 2 ) INFORMATION FOR SEQ ID NO:23:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

AGCAACTGCC AGATGGC                                                              17

( 2 ) INFORMATION FOR SEQ ID NO:24:

( i ) SEQUENCE CHARACTERISTICS:

(A) LENGTH: 11 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:24:

AATTGAGATT C                                                                11

(2) INFORMATION FOR SEQ ID NO:25:

(i) SEQUENCE CHARACTERISTICS:
   (A) LENGTH: 11 base pairs
   (B) TYPE: nucleic acid
   (C) STRANDEDNESS: single
   (D) TOPOLOGY: linear (ii) MOLECULE TYPE: DNA (genomic)

(xi) SEQUENCE DESCRIPTION: SEQ ID NO:25:

AATTGAGATG C                                                                11

We claim:

1. An isolated DNA segment consisting essentially of the nucleotide sequence set forth in SEQ ID NO:3.

2. A recombinant DNA expression vector which comprises, in operable linkage, an enhancer sequence consisting essentially of the nucleotide sequence set forth in SEQ ID NO:3, a promoter sequence and at least one gene encoding a protein of interest.

3. A murine host cell transformed with the DNA expression vector of claim 2, said host cell selected from the group consisting of B cells and cells of the B lineage.

* * * * *